United States Patent
Riggins et al.

(10) Patent No.: US 11,110,079 B2
(45) Date of Patent: Sep. 7, 2021

(54) MEBENDAZOLE POLYMORPH FOR TREATMENT AND PREVENTION OF TUMORS

(71) Applicant: THE JOHNS HOPKINS UNIVERSITY, Baltimore, MD (US)

(72) Inventors: Gregory Riggins, White Hall, MD (US); Renyuan Bai, Joppa, MD (US); Verena Staedtke, Baltimore, MD (US); Avadhut D. Joshi, Baltimore, MD (US); Tara Williamson, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 15/548,959

(22) PCT Filed: Feb. 8, 2016

(86) PCT No.: PCT/US2016/016968
§ 371 (c)(1),
(2) Date: Aug. 4, 2017

(87) PCT Pub. No.: WO2016/127168
PCT Pub. Date: Aug. 11, 2016

(65) Prior Publication Data
US 2018/0021310 A1    Jan. 25, 2018

Related U.S. Application Data

(60) Provisional application No. 62/112,706, filed on Feb. 6, 2015.

(51) Int. Cl.
*A61K 31/4184* (2006.01)
*A61K 9/16* (2006.01)
(Continued)

(52) U.S. Cl.
CPC .......... *A61K 31/4184* (2013.01); *A23L 33/10* (2016.08); *A61K 9/0056* (2013.01);
(Continued)

(58) Field of Classification Search
None
See application file for complete search history.

(56) References Cited

U.S. PATENT DOCUMENTS 7,423,015 B1 * 9/2008 Chada ................ A61K 31/4439
514/1.1
2011/0144043 A1 * 6/2011 Frank .................. A61K 31/381
514/26

FOREIGN PATENT DOCUMENTS

CA      2342470 A1 * 9/2002  ......... A61K 31/4184

OTHER PUBLICATIONS

Clinicaltrials.gov ([retrieved from on-line website: https://clinicaltrials.gov/ct2/show/NCT01350271, published in 2013] (Year: 2013).*
(Continued)

*Primary Examiner* — Kyung S Chang
(74) *Attorney, Agent, or Firm* — Casimir Jones, S.C.

(57) ABSTRACT

Mebendazole is an antiparasitic drug with over 40 years of safe use. Recently mebendazole was repurposed for glioblastoma therapy. Three polymorphs of mebendazole exist, but the relative polymorph content for existing drugs varies, and the therapeutic anti-cancer relevance of the different polymorphs was unknown. As an oral drug mebendazole polymorph C is a superior form, and it reaches the brain and brain tumors in effective concentrations. Efficacy is further improved by combining mebendazole with a P-glycoprotein inhibitor. Mebendazole may also be used for therapy of other cancers, as well as a chemo-preventative agent.

7 Claims, 17 Drawing Sheets

Figure 3B:
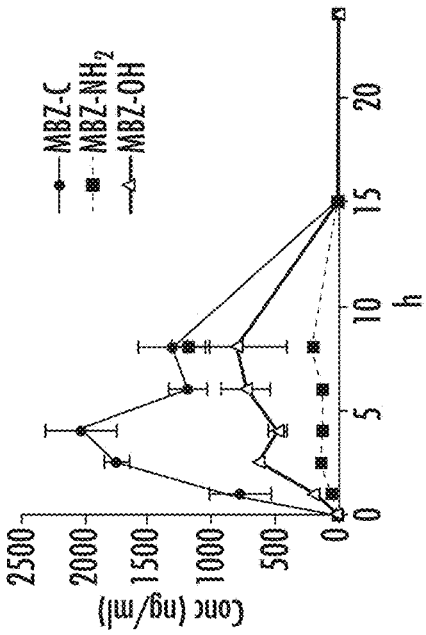

(51) Int. Cl.
| | |
|---|---|
| A61K 9/00 | (2006.01) |
| A61K 9/50 | (2006.01) |
| A61K 31/192 | (2006.01) |
| A61K 31/473 | (2006.01) |
| A61K 45/06 | (2006.01) |
| A23L 33/10 | (2016.01) |
| A61P 35/00 | (2006.01) |
| G01N 21/35 | (2014.01) |

(52) U.S. Cl.
CPC ............. *A61K 9/1605* (2013.01); *A61K 9/50* (2013.01); *A61K 31/192* (2013.01); *A61K 31/473* (2013.01); *A61K 45/06* (2013.01); *A23V 2002/00* (2013.01); *A61P 35/00* (2018.01); *C07B 2200/13* (2013.01); *G01N 21/35* (2013.01)

(56) References Cited

OTHER PUBLICATIONS

Kachrimanis, K., et al., "Simultaneous quantitative analysis of mebendazole polymorphs A—C in powder mixtures by DRIFTS spectroscopy and ANN modeling" Journal of Pharmaceutical and Biomedical Analysis 51 (2010) 512-520.
Breedveld, P., et al., "Use of P-glycoprotein and BCRP inhibitors to improve oral bioavailability and CNS penetration of anticancer drugs" Trends in Pharmacological Sciences vol. 27 No. 1 Jan. 2006.
Scheper, M., et al., "Sulindac Induces Apoptosis and Inhibits Tumor Growth In Vivo in Head and Neck Squamous Cell Carcinoma" Neoplasia . vol. 9, No. 3, Mar. 2007, pp. 192-199.
Mukhopadhyay, T., et al., "Mebendazole Elicits a Potent Antitumor Effect on Human Cancer Cell Lines Both in Vitro and in Vivo" Clinical Cancer Research vol. 8, 2963-2969, Sep. 2002.
Bai, R., "Brain Penetration and Efficacy of Different Mebendazole Polymorphs in a Mouse Brain Tumor Model" Clin Cancer Res. Aug. 1, 2015; 21(15): 3462-3470.
Agarwal S, Manchanda P, Vogelbaum M A, Ohlfest J R, Elmquist W F. Function of the blood-brain barrier and restriction of drug delivery to invasive glioma cells: findings in an orthotopic rat xenograft model of glioma. Drug Metab Dispos 2013; 41: 33-9.
Bai R Y, Staedtke V, Aprhys C M, Gallia G L, Riggins G J. Antiparasitic mebendazole shows survival benefit in 2 preclinical models of glioblastoma multiforme. Neuro Oncol 2011; 13: 974-82.
Bai R Y, Staedtke V, Lidov H G, Eberhart C G, Riggins G J. OTX2 Represses Myogenic and Neuronal Differentiation in Medulloblastoma Cells. Cancer Res 2012; 72: 5988-6001.
Bai R Y, Staedtke V, Rudin C M, Bunz F, Riggins G J. Effective treatment of diverse medulloblastoma models with mebendazole and its impact on tumor angiogenesis. Neuro Oncol Sep. 24, 2014; , 545-554, Epub ahead of print.
Brits M, Liebenberg W, de Villiers M M. Characterization of polymorph transformations that decrease the stability of tablets containing the WHO essential drug mebendazole. J Pharm Sci 2010; 99: 1138-51.
Dakshanamurthy S, Issa N T, Assefnia S, et al. Predicting new indications for approved drugs using a proteochemometric method. J Med Chem 2012; 55: 6832-48.
Doudican N, Rodriguez A, Osman I, Orlow S J. Mebendazole induces apoptosis via Bcl-2 inactivation in chemoresistant melanoma cells. Mol Cancer Res 2008; 6: 1308-15.
Garcia-Rodriguez et al., "Changed crystallinity of mebendazole solid dispersion: improved anthelmintic activity" Int J Pharm. Jan. 17, 2011;403(1-2):23-8.
Minocha M, Khurana V, Qin B, Pal D, Mitra A K. Enhanced brain accumulation of pazoparnib by modulating P-gp and Bcrp1 mediated efflux with canertinib or erlotinib. Int J Pharm 2012; 436: 127-34.
Nygren P, Fryknas M, Agerup B, Larsson R. Repositioning of the anthelmintic drug mebendazole for the treatment for colon cancer. J Cancer Res Clin Oncol 2013; 139: 2133-40.
Rodriguez-Caabeiro F, Criado-Fornelio A, Jimenez-Gonzalez A, et al. Experimental chemotherapy and toxicity in mice of three mebendazole polymorphic forms. Chemotherapy 1987; 33: 266-71.
Sane R, Agarwal S, Elmquist W F. Brain distribution and bioavailability of elacridar after different routes of administration in the mouse. Drug Metab Dispos 2012; 40: 1612-9.
Swanepoel E, Liebenberg W, de Villiers M M. Quality evaluation of generic drugs by dissolution test: changing the USP dissolution medium to distinguish between active and non-active mebendazole polymorphs. Eur J Pharm Biopharm 2003; 55: 345-9.
Tang S C, Lagas J S, Lankheet N A, et al. Brain accumulation of sunitinib is restricted by P-glycoprotein (ABCB1) and breast cancer resistance protein (ABCG2) and can be enhanced by oral elacridar and sunitinib coadministration. Int J Cancer 2012; 130: 223-33.
Tang S C, Nguyen L N, Sparidans R W, Wagenaar E, Beijnen J H, Schinkel A H. Increased oral availability and brain accumulation of the ALK inhibitor crizotinib by coadministration of the P-glycoprotein (ABCB1) and breast cancer resistance protein (ABCG2) inhibitor elacridar. Int J Cancer 2014; 134: 1484-94.
Office Action of related CN 201680014427.4, dated Dec. 16, 2020, 7 pages.
Charoenlarp P, Waikagul J, Muennoo C, Srinophakun S, Kitayaporn D. Efficacy of single-dose mebendazole, polymorphic forms A and C, in the treatment of hookworm and Trichuris infections. Southeast Asian J Trop Med Public Health 1993; 24: 712-6.
Doudican N A, Byron S A, Pollock P M, Orlow S J. XIAP downregulation accompanies mebendazole growth inhibition in melanoma xenografts. Anticancer Drugs 2013; 24: 181-8.
Liebenberg W, Dekker T G, Lotter A P, de Villiers M M. Identification of the mebendazole polymorphic form present in raw materials and tablets available in South Africa. Drug Dev Ind Pharm 1998; 24: 485-8.

* cited by examiner

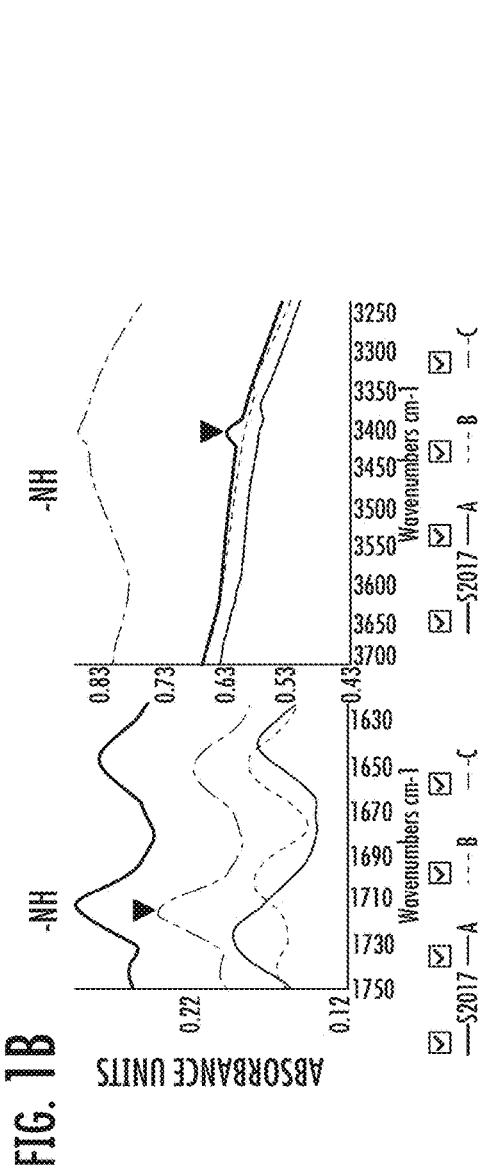
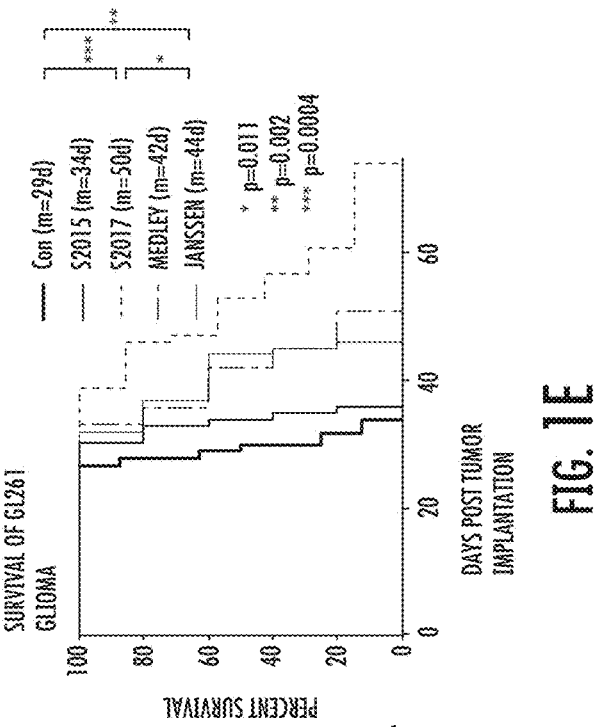
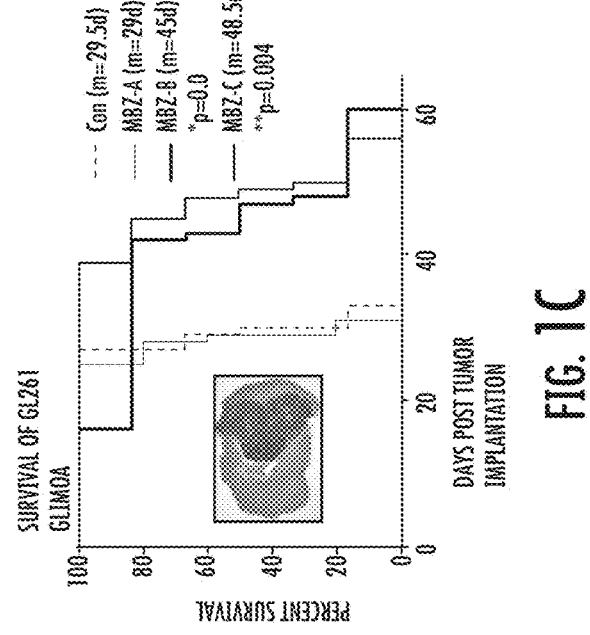

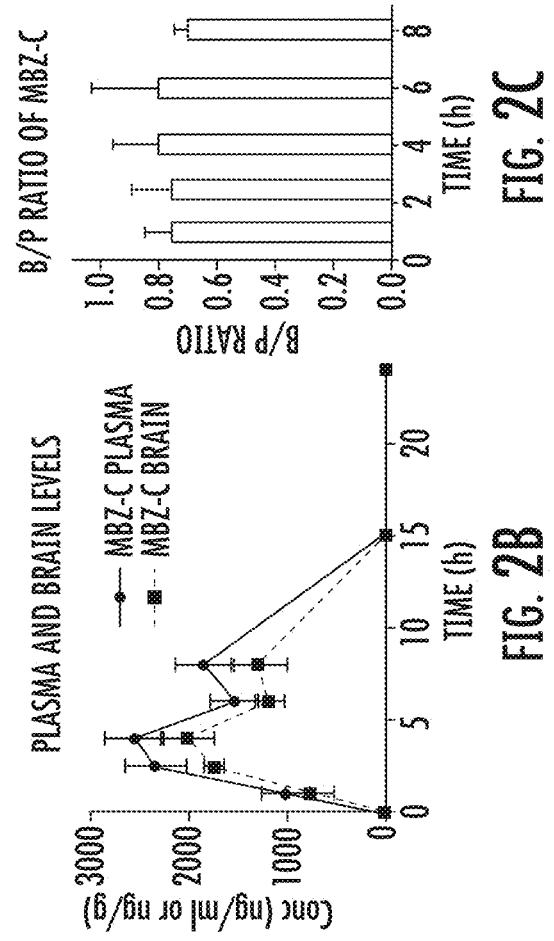
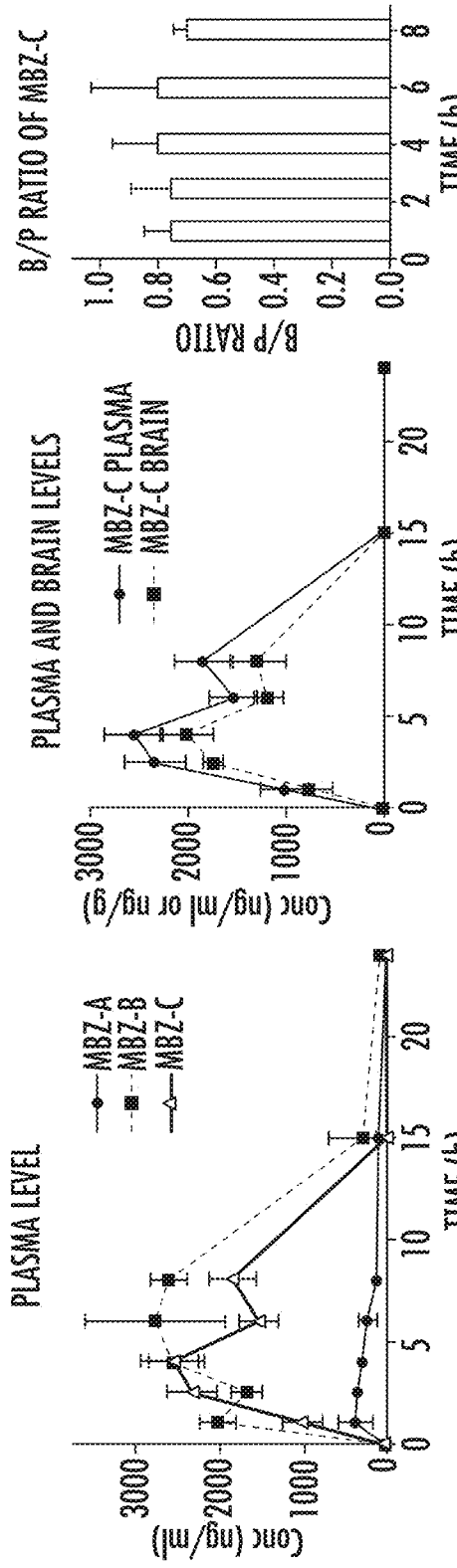
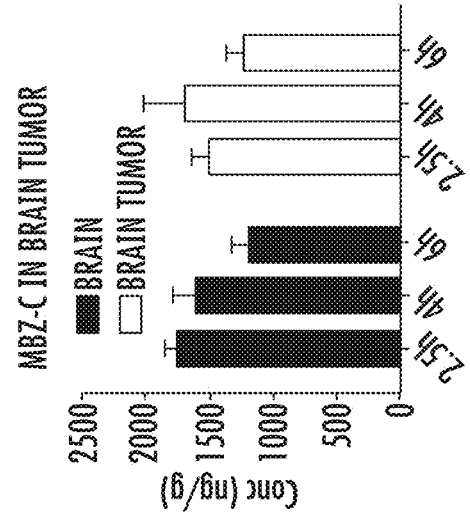
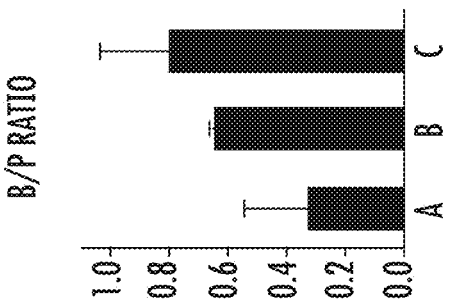
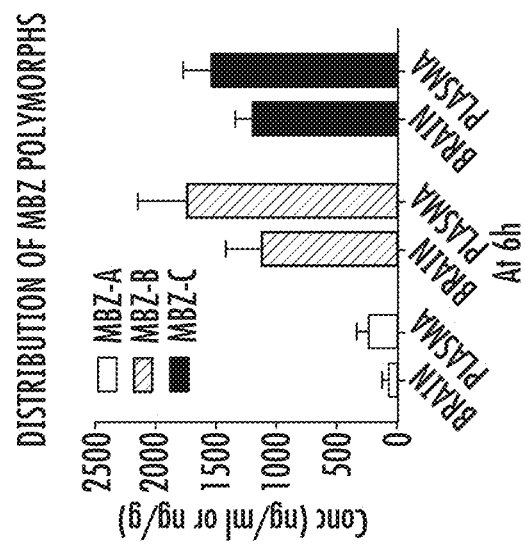

D425 MEDULLOBLASTOMA XENOGRAFT

FIG. 6A

| POLYMORPH | DETECTION | PLASMA | | | | BRAIN | | | | B/P |
|---|---|---|---|---|---|---|---|---|---|---|
| | | $T_{1/2}(h)$ | $T_{max}$ (h) | $C_{max}$ (ng/ml) | $AUC_{0-24h}$ (h*ng/ml) | $T_{1/2}(h)$ | $T_{max}$ (h) | $C_{max}$ (ng/g) | $AUC_{0-24h}$ (h*ng/g) | |
| A | MBZ | 3.23 | 1 | 379.3 | 3052 | | | | | |
| B | MBZ | 3.18 | 6 | 2778.3 | 26474 | 1.64 | 4 | 2016 | 13134 | 0.82 |
| C | MBZ | 0.90 | 4 | 2553.3 | 16039 | | | | | |
| A | MBZ-NH2 | | 2.5 | 201.3 | 2841 | | | | | |
| B | MBZ-NH2 | | 8 | 1656.7 | 18583 | | 8 | 201.6 | 1336 | 0.13 |
| C | MBZ-NH2 | | 8 | 1416.7 | 10516 | | | | | |
| A | MBZ-OH | | 1 | 32.1 | 247 | | | | | |
| B | MBZ-OH | | 8 | 744.7 | 4970 | | 8 | 794.3 | 5427 | 0.94 |
| C | MBZ-OH | | 6 | 951.7 | 5781 | | | | | |

FIG. 6B

| DRUG | DETECTION | PLASMA | | | BRAIN | | | B/P $AUC_{0-8h}$ | SIGNIFICANT? |
|---|---|---|---|---|---|---|---|---|---|
| | | $T_{max}$ (h) | $C_{max}$ (ng/mL) | $AUC_{0-8h}$ (h*ng/ml) | $T_{max}$ (h) | $C_{max}$ (ng/g) | $AUC_{0-8h}$ (h*ng/g) | | |
| MBZ | MBZ | 4 | 2553.3 | 15340 | 4 | 2016.0 | 11510 | 0.75 | NO |
| ELD + MBZ | MBZ | 2.5 | 1433.3 | 8636 | 2.5 | 1459.7 | 8904 | 1.03 | |
| MBZ | MBZ-NH2 | 8 | 1416.7 | 8264 | 8 | 201.6 | 1010 | 0.12 | YES |
| ELD + MBZ | MBZ-NH2 | 2.5 | 1191.7 | 7826 | 8 | 387.8 | 2386 | 0.30 | |
| MBZ | MBZ-OH | 2.5 | 810.0 | 4679 | 8 | 794.3 | 4135 | 0.88 | NO |
| ELD + MBZ | MBZ-OH | 2.5 | 491.0 | 2680 | 2.5 | 712.6 | 3475 | 1.30 | |

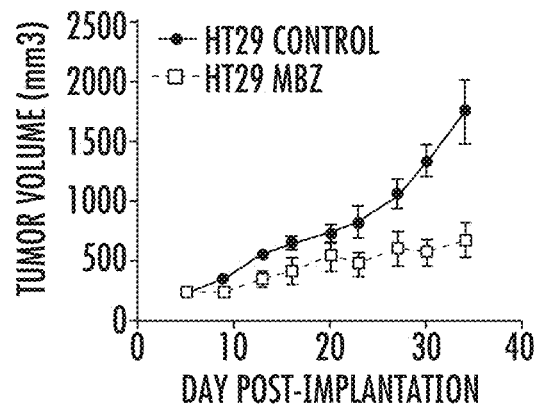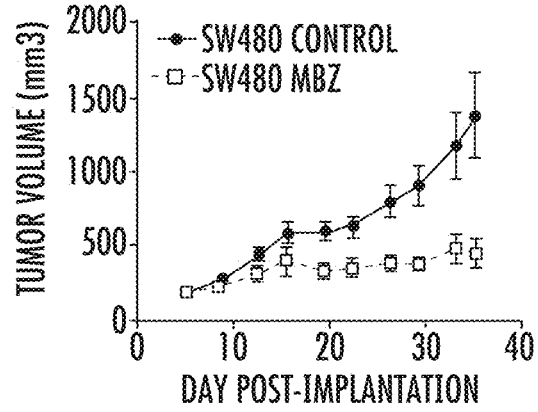
FIG. 9A  FIG. 9B
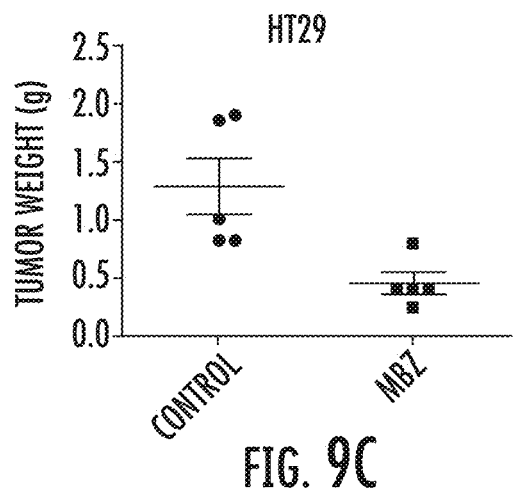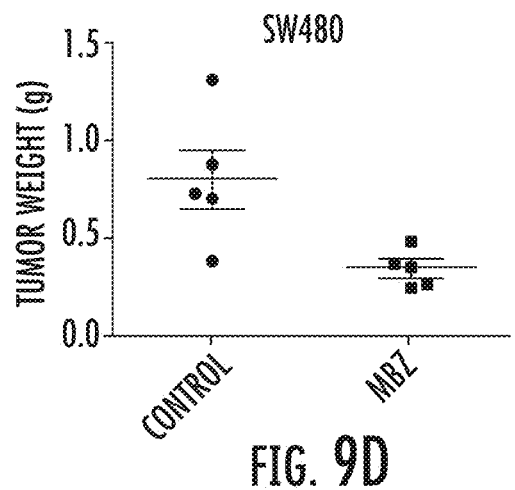
FIG. 9C  FIG. 9D
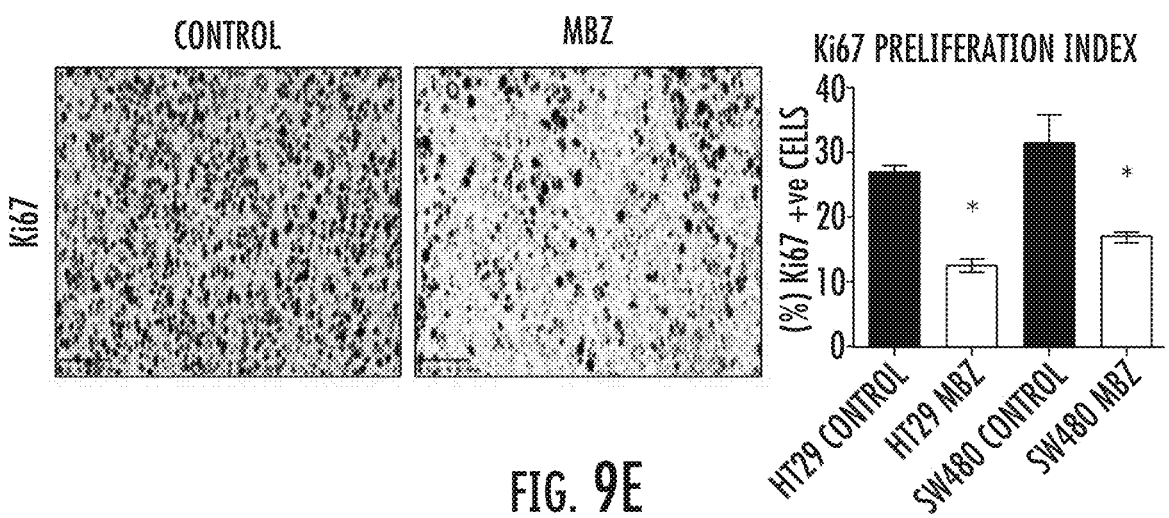
FIG. 9E

TABLE 1:

| GROUP | REGION | | | TOTAL (% INHIBITION) | POLYP SIZE (mm) | | | |
|---|---|---|---|---|---|---|---|---|
| | PROXIMAL | MIDDLE | DISTAL | COLON | | < 1.0 | 1.0-2.0 | 2.1-3.0 | > 3.0 |
| UNTREATED CONTROL | 15.5±2.28 | 28.83±3.74 | 16.92±2.37 | 1.25±0.33 | 62.5 | 32.76 | 19.83 | 7.25 | 2.67 |
| MEBENDAZOLE 35mg/kg FEED | 4.58±0.65 | 12.42±1.22 | 9.83±1.4 | 0.42±0.19 | 27.25 (56%) | 10.63 | 12 | 4.46 | 0.45 |
| SULINDAC 160 p.p.m. DRINKING WATER | 4.77±0.68 | 6.08±0.94 | 3.62±0.53 | 1.54±0.35 | 16 (74%) | 8.46 | 6.08 | 1.23 | 0.15 |
| MBZ 35mg/kg + SULINDAC 160 p.p.m. | 2.42±0.41 | 2.42±0.37 | 1.37±0.29 | 0.37±0.14 | 6.58 (90%) | 3.73 | 2.58 | 0.22 | 0.05 |

FIG. 10D

ADDITIONAL STATISTICAL ANALYSIS

| | PROXIMAL | P VALUE | MIDDLE | P VALUE | DISTAL | P VALUE | COLON | P VALUE |
|---|---|---|---|---|---|---|---|---|
| UNTREATED CONTROL | 15.5(±2.28) | | 28.83(±3.74) | | 16.92(±2.37) | | 1.25(±0.33) | |
| 35mg/kg MBZ FEED | 4.58(±0.65) | 0.0001 | 12.42(±1.22) | 0.0004 | 9.83(±1.40) | 0.0174 | 0.42(±0.19) | 0.0397 |
| 160 ppm SULINDAC | 4.77(±0.68) | 0.0001 | 6.08(±0.94) | <0.0001 | 3.62(±0.53) | <0.0001 | 1.54(±0.35) | <0.5562 |
| 35mg/kg MBZ + 160ppm SULINDAC | 2.42(±0.41) | <0.0001 | 2.42(±0.37) | <0.0001 | 1.37(±0.29) | <0.0001 | 0.37(±0.14) | <0.0083 |
| | SUL VS MBZ/SUL | 0.0037 | SUL VS MBZ/SUL | 0.0003 | SUL VS MBZ/SUL | 0.0003 | SUL VS MBZ/SUL | 0.0014 |

POLYP COUNTS (+/-SEM)

FIG. 11C

MEBENDAZOLE POLYMORPH FOR TREATMENT AND PREVENTION OF TUMORS

CROSS-REFERENCE TO RELATED APPLICATIONS

This application is a 35 U.S.C. § 371 U.S. national entry of International Application PCT/US2016/016968, having an international filing date of Feb. 8, 2016, which claims the benefit of U.S. Provisional Application No. 62/112,706, filed Feb. 6, 2015, the content of each of the aforementioned applications is herein incorporated by reference in their entirety.

This invention was made with government support under R25NS065729 awarded by National Institute of Neurological Disorders and Stroke, and P30 -CA006973, UL1-RR025005 and 1S10RR026824-01 from the National Institutes of Health. The government has certain rights in the invention.

TECHNICAL FIELD OF THE INVENTION

This invention is related to the area of pharmacology. In particular, it relates to cancer therapeutics.

BACKGROUND OF THE INVENTION

Central nervous system (CNS) cancers are difficult to treat because most systemically administered therapeutics fail to reach effective concentrations in intracranial tumors (1). This is partially explained by the blood-brain barrier (BBB). In the CNS, the BBB exists along all capillaries consisting of tight junctions thereby blocking large and hydrophilic molecules from passing to the CNS tissues. It is estimated that only about 2% of small-molecule drugs are able to effectively cross the BBB (2).

Mebendazole (MBZ) has been safely used as an antiparasitic in humans for over four decades and displays efficacy against intracranial helminthic infections. We recently demonstrated MBZ preclinical efficacy in orthotopic glioma and medulloblastoma rodent models (3, 4). MBZ significantly reduced tumor growth and improved survival of brain tumor-bearing mice. Based on these results, a Phase I clinical trial with a dose escalation of MBZ for newly diagnosed high-grade glioma patients has been initiated (NCT01729260). Evidence has been generated supporting several anti-cancer mechanisms for MBZ, including tubulin-binding, kinase inhibition anti-angiogenesis and pro-apoptosis (3-8). However, the important features of MBZ's brain penetration and pharmacokinetics remain to be determined. This understanding is important to potentially improve the clinical use of MBZ.

MBZ is highly hydrophobic and can form three different polymorphs based on crystallization conditions (9). The polymorphs A, B and C (MBZ-A, B and C) displayed distinct features in solubility, toxicity and therapeutic effects in anthelmintic applications (10-12). The difference in anti-tumor efficacy of the three polymorphs has not yet been investigated, however, this information might be crucial to future MBZ cancer therapies, since drug formulations might contain various polymorphs in different amounts or combinations. Another critical reason for further investigation is that polymorph C, the most efficacious polymorph in anthelmintic use, can transform over time to the less effective polymorph A, especially with higher temperatures and humidity (13). Since the polymorphs only exist in the solid form and MBZ is exclusively an oral drug, studying the relevant anti-tumor properties of different polymorphs is best accomplished by determining bioavailability and efficacy in animal models via oral administration of MBZ polymorphs. There is a continuing need in the art to identify more effective, more consistent, and safer therapeutics for treating cancers, in particular brain cancers.

SUMMARY OF THE INVENTION

According to one aspect of the invention a pharmaceutical formulation of mebendazole is provided. At least 90% of the mebendazole in the formulation is polymorph C, and the formulation is granulated.

According to another aspect of the invention a pharmaceutical formulation of mebendazole is provided that comprises polymorph C and an inhibitor of P-glycoprotein.

According to another aspect of the invention a pharmaceutical formulation that comprises mebendazole and a non-steroidal anti-inflammatory drug (NSAID) is provided.

Another aspect of the invention is a method of administering a pharmaceutical mebendazole formulation. The pharmaceutical mebendazole formulation can be a granulated formulation in which at least 90% of the mebendazole in the formulation is polymorph C, or it can be a combination formulation of polymorph C and an inhibitor of P-glycoprotein, or it can be a formulation of mebendazole comprising polymorph C and an NSAID. According to the method, the formulation is applied to a food prior to ingestion of the food.

According to still another aspect of the invention a method is provided to monitor anti-cancer potency of a mebendazole pharmaceutical formulation. A pharmaceutical formulation comprising mebendazole is assayed, and the amount of polymorph C and amount of polymorph A are determined.

Another aspect of the invention is a method of treating a tumor or reducing the risk of developing a tumor in a human. A pharmaceutical formulation of mebendazole, whether a granulated formulation in which at least 90% of the mebendazole is polytnorph C, or a combination formulation of polymorph C and an inhibitor of P-glycoprotein, or a combination formulation of polymorph C and an NSAID, is administered or dispensed to a human for oral ingestion. The human either has a tumor or is at elevated risk of developing a tumor.

An additional aspect of the invention is a kit for treating tumors or reducing the risk of developing tumor(s). The kit comprises (a) mebendazole (optionally comprising polymorph C) and (b) an inhibitor of P-glycoprotein or an NSAID.

Yet another aspect of the invention is a method of treating a tumor in a human or reducing the risk of developing a tumor. Mebendazole (optionally comprising polymorph C) and either an inhibitor of P-glycoprotein or an NSAID are administered or dispensed to the human for oral ingestion.

These and other embodiments which will be apparent to those of skill in the art upon reading the specification provide the art with tools for combatting highly refractory cancers.

BRIEF DESCRIPTION OF THE DRAWINGS

FIGS. 1A-1E. MBZ-C is the most efficacious polymorph with limited toxicity FIG. 1A and FIG. 1B. Infra-red spectra of MBZ polymorphs and MBZ tablets from different suppliers: S2015 and S2017 (Aurochem), Teva (after 2-year storage at RT), Medley and Janssen. Two peaks represent the —NH and —C=O groups in the molecules. Black arrow heads indicate the peaks of MBZ-C control.

FIG. 1C. Kaplan Meier survival curves and Luceiferase counts. Kaplan Meier survival curves of mice implanted with GL261-luc glioma and treated with different MBZ polymorphs (A, B and C). An H&E staining of the GL261-luc glioma-bearing mouse brain by coronal cut was shown. 5 days after the tumor implantation, the mice were gavaged with MBZ and control animals were feed with vehicles. One mouse in the MBZ-B group presumably died from drug toxicity as no significant tumor was found in the brain. The p-values of Con vs MBZ-B and Con vs MBZ-C are indicated. The p-value of MBZ-B vs MBZ-C is 0.72. m: median survival in days. Con: n=6; MBZ-A: n=5; MBZ-B: n=6; MBZ-C: n=6.

FIG. 1D. Luciferase counts measured by Xenogen reflected the size of GL261-luc brain tumor in mice treated with MBZ polymorphs for 20 days.

FIG. 1E. Survival curves of GL261-luc bearing mice treated with MBZ tablets from different suppliers. Con: n=6; S2015: n=5; S2017: n=6; Medley: n=5; Janssen: n=5.

FIGS. 2A-2F. Plasma and brain distributions of MBZ polymorphs

FIG. 2A. A time course of the MBZ plasma levels in C57BL6 mice after oral gavage of MBZ-A, B or C at 50 mg/kg.

FIG. 2B. Brain and plasma levels of MBZ-C in a time course after oral gavage at 50 mg/kg. Animals were thoroughly perfused with PBS for all brain distribution studies.

FIG. 2C. Brain/plasma (B/P) ratios of MBZ-C. Data were collected from three mice at each time point.

FIG. 2D. Brain and plasma levels of MBZ polymorphs at 6 h following oral gavage (50 mg/kg). B/P ratio of MBZ polymorphs at 6 h following oral gavage.

FIG. 2E. The mean B/P ratio of MBZ-A is 0.32, MBZ-B is 0.64 and MBZ-C is 0.80.

FIG. 2F. MBZ-C distributed equally in the brain and brain tumor. GL261 tumors implanted in the right side of mouse frontal lobe were resected and compared with the contralateral normal brain tissue.

FIGS. 3A-3D. Distribution of MBZ Metabolites

Figure 3D:
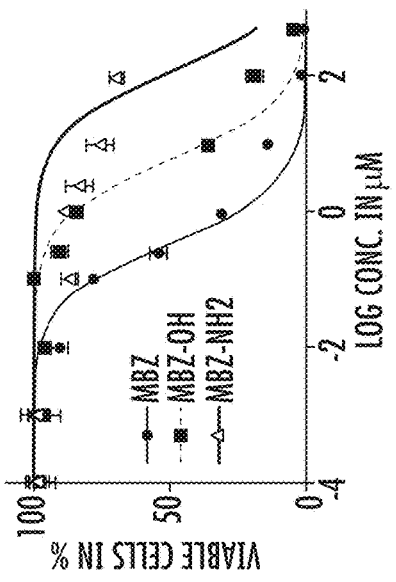

FIG. 3A-FIG. 3D. The plasma (FIG. 3A and FIG. 3C) and brain (FIG. 3B and FIG. 3C) levels of MBZ and its metabolites, MBZ-OH (rac dihydro mebendazole, CAS 60254-95-7) and MBZ-NH2 (2-amino-5-benzoyl-benzimidazole, CAS 52329-60-9), were analyzed following oral gavage of 50 mg/kg MBZ-C. FIG. 3D shows inhibition ($IC_{50}$ curve) of GL261 by MBZ and its metabolites.

Figure 4A:
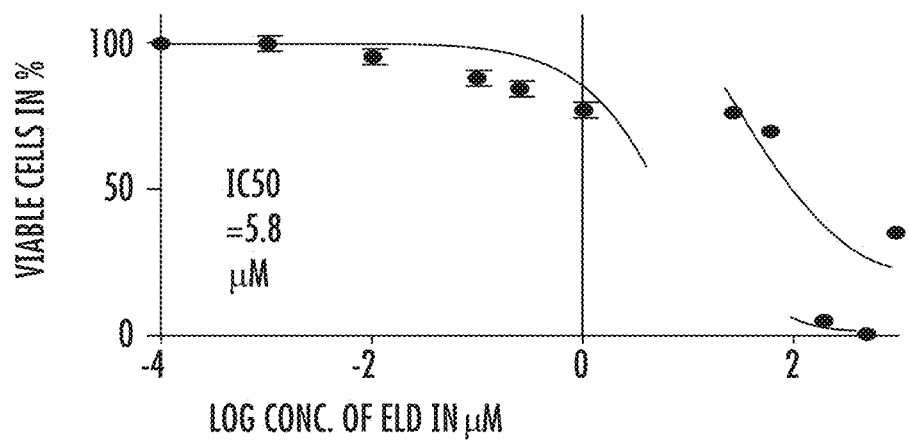
Figure 4B:
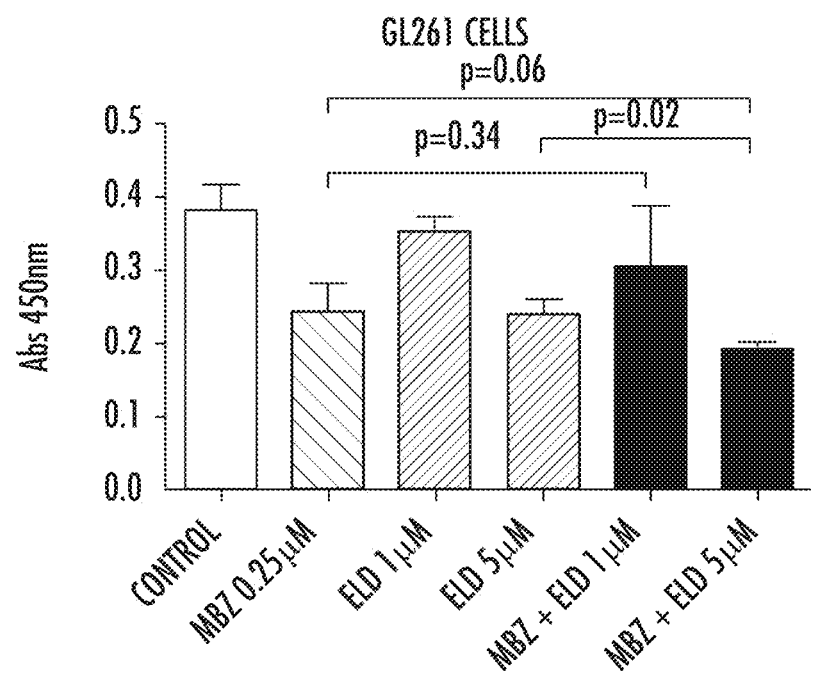
Figure 4C:
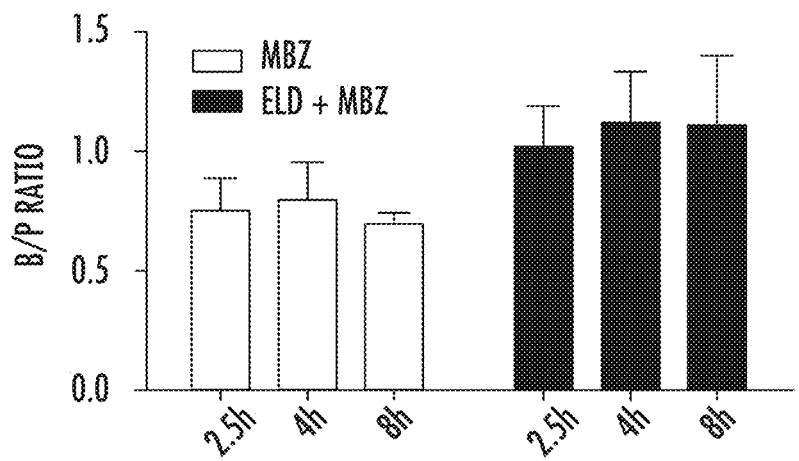

FIGS. 4A-4C. Combination of MBZ with elacridar

FIG. 4A. $IC_{50}$ curve of GL261 glioma cells with elacridar (HD). $IC_{50}$=5.8 μM.

FIG. 4B. Inhibition of GL261 cells by MBZ (0.25 μM), ELD (1 or 5 μM) or the combination. Cells were incubated with the indicated drugs for 72 h and the living cells were measured by the colorimetric assay.

FIG. 4C. ELD elevated the average B/P ratios of MBZ in mice.

FIGS. 5A-5D. Combination of MBZ with elacridar improved the efficacy

Figure 5A:
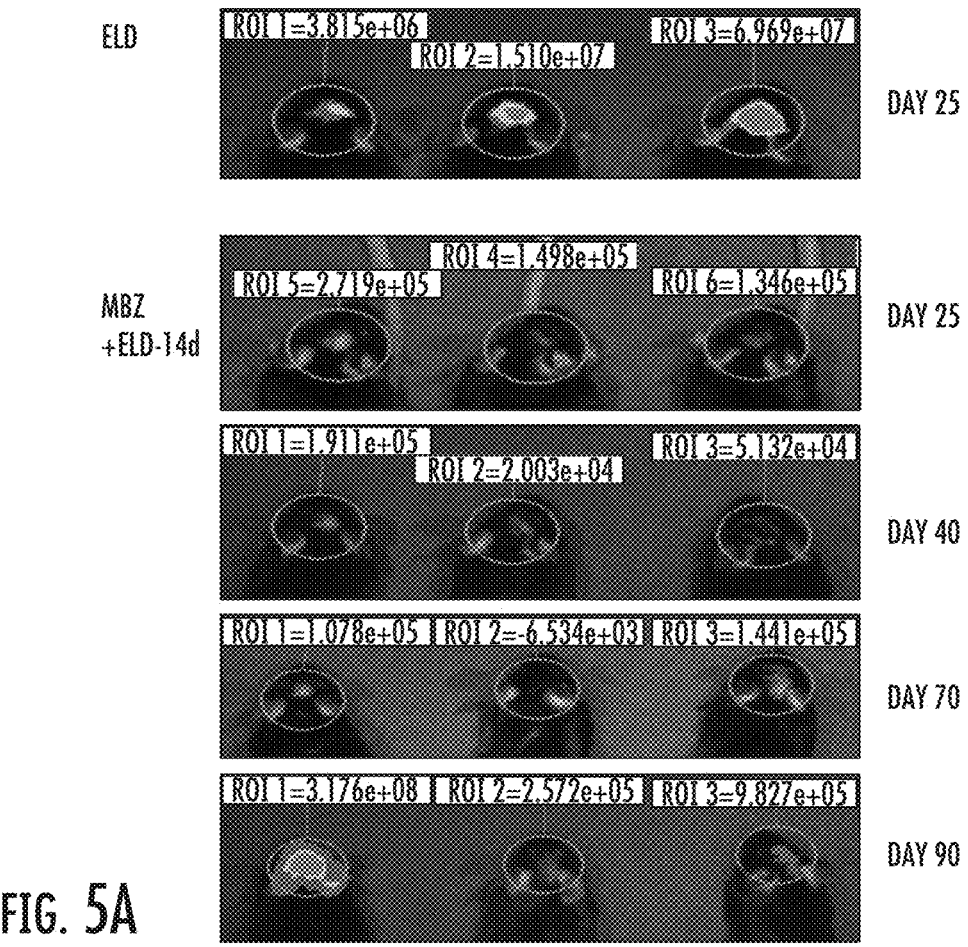
Figure 5B:
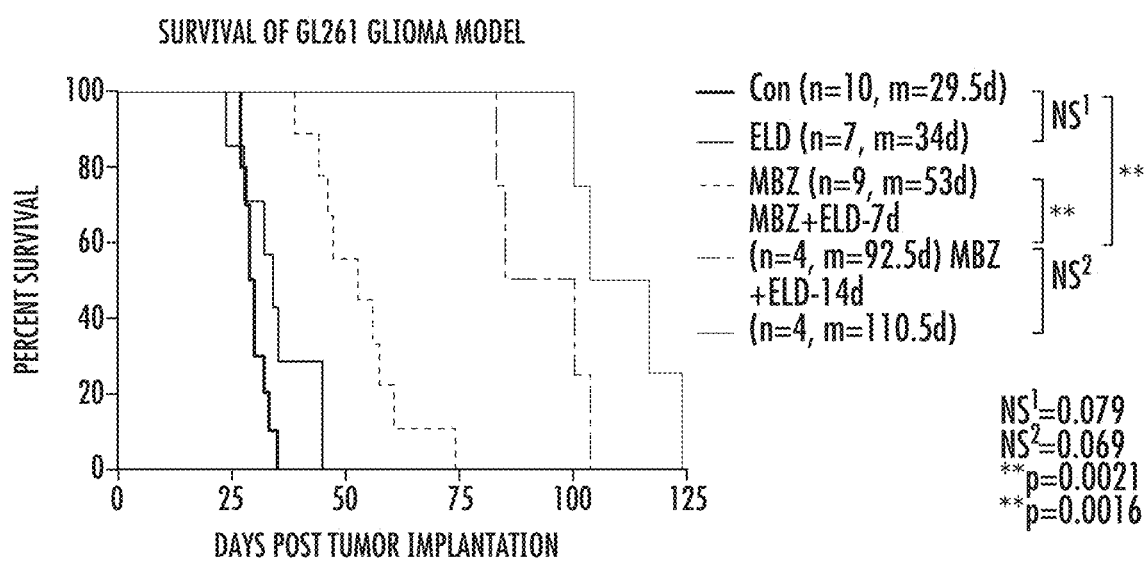

FIG. 5A and FIG. 5B. GL261 cells transfected with luciferase were implanted in C57BL6 mice and the treatments were initiated 5 days after the implantation. Elaridar (ELD) was oral gavaged at 50 mg/kg 2 hours before the MBZ administration (50 mg/kg) for the first 7 or 14 days of treatment. Thereafter, MBZ was given five days a week at the same dose for the rest of the therapy. The ELD alone group was gavaged with ELD for 14 daily doses. Animals treated by MBZ and ELD were monitored by Xenogen for tumor luciferase signals starting from 25 days after the tumor implantation (FIG. 5A).

Figure 5C:
Figure 5D:
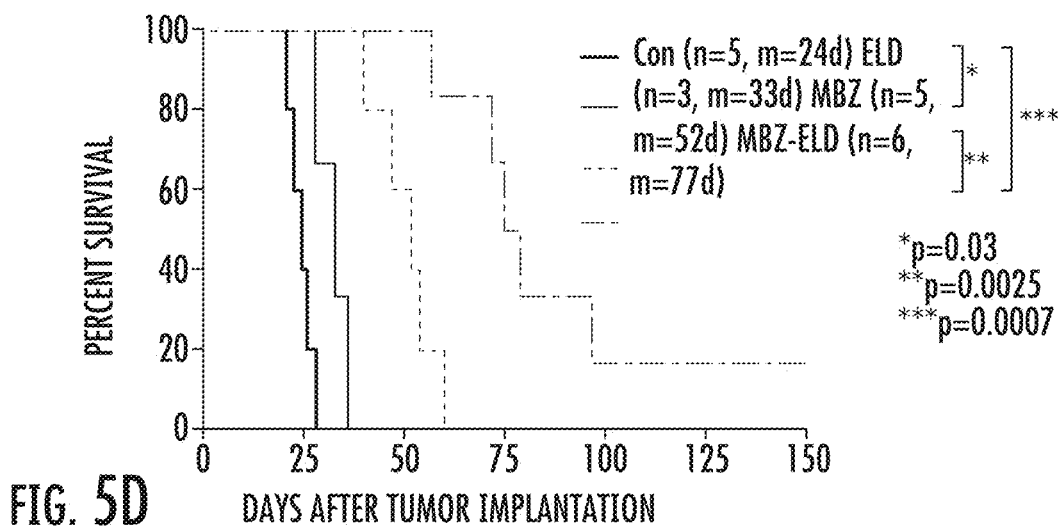

FIG. 5C and FIG. 5D. D425 medulloblastoma cells were implanted in the mouse cerebellum and formed a cerebellar tumor (FIG. 5C, H&E staining). Five days after the tumor implantation, mice were treated with vehicle (Con), 7 days of 50 mg/kg elacridar (ELD), 7 days of ELD with 50 mg/kg MBZ-C five days a week (MBZ-ELD) or MBZ-C alone (MBZ).

FIGS. 6A-6B. (Table 1.) Table 1. Pharmacokinetics of MBZ polymorphs in mice.

FIG. 6A. Using LS-MS, MBZ and the metabolites MBZ-NH2 and MBZ-OH were measured in plasma samples of mice orally gavaged with the indicated MBZ polymorphs. In terms of the plasma AUC24 h, it is B>C>A with p<0.05.

FIG. 6B. Pharmacokinetics of MBZ-C and metabolites in mice gavaged with MBZ or the combination of MBZ and elacridar (ELD).

Figure 7:
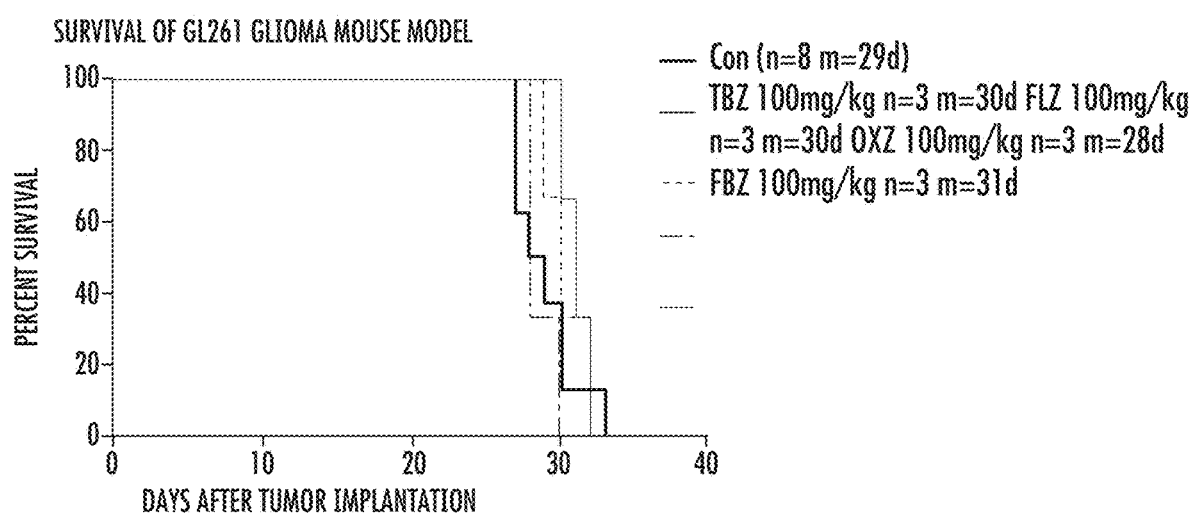

FIG. 7. Test of benzimidazoles in GL261 glioma mouse model. GL261-luc glioma-bearing mice were treated with thiabendazole (TBZ), flubendazole (FLZ), oxifendazole (OXZ), fenbendazole (FBZ) at 100 mg/kg via oral gavage, starting from day 5 after the tumor implantation. All the differences in survival are not significant in Mantel-Cox test. n: number of mice; m: median survival in days.

Figure 8:
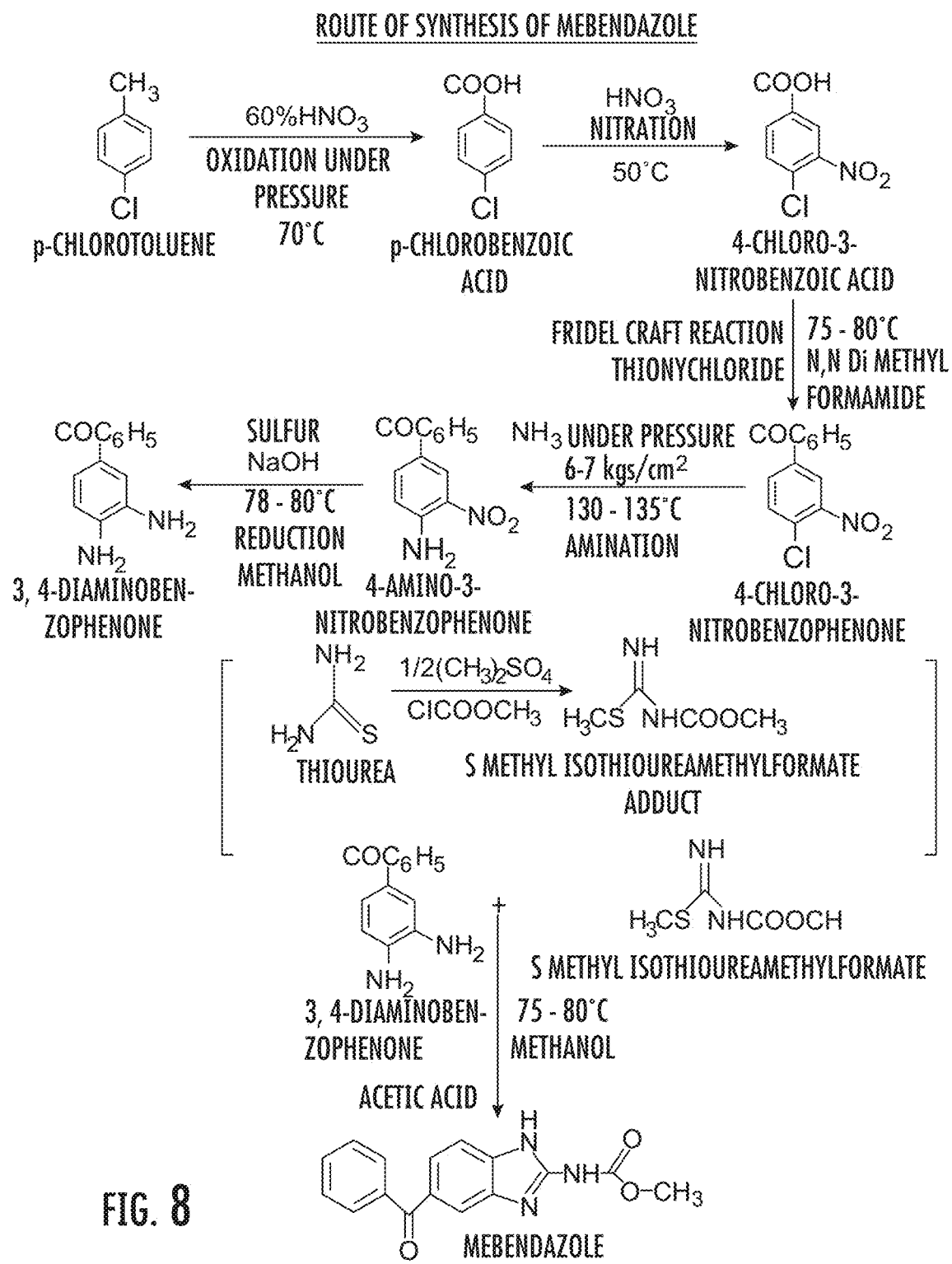

FIG. 8. A synthesis scheme for making mebendazole.

FIGS. 9A-9E. Oral Mebendazole inhibits growth and proliferation in two different colon cancer flank cell line xenografts. Two human colorectal carcinoma cell lines, HT29 and SW480, were implanted subcutaneously into the flanks of Nude mice and treated for four weeks with 50 mg/kg MBZ by oral gavage. Tumor volumes were measured twice weekly, averaged, and plotted over the course of the experiment. HT29 xenograft (FIG. 9A) and SW480 xenograft (B) growth inhibitory curves. Resected flank tumors from each group were weighed at the end of the experiment and compared to untreated control (FIG. 9C, FIG. 9D) Paraffin-embedded flank tumor tissues were stained for Ki67 proliferation marker. The MBZ treated tissue showed significantly less positive (brown nuclei) staining in both models (FIG. 9E). Five randomly selected fields from each slide were quantified as the percent Ki67-positive cell×100/total number of cells and represent the mean+SEM of five animals. *, P<0.05.

Figure 10A:
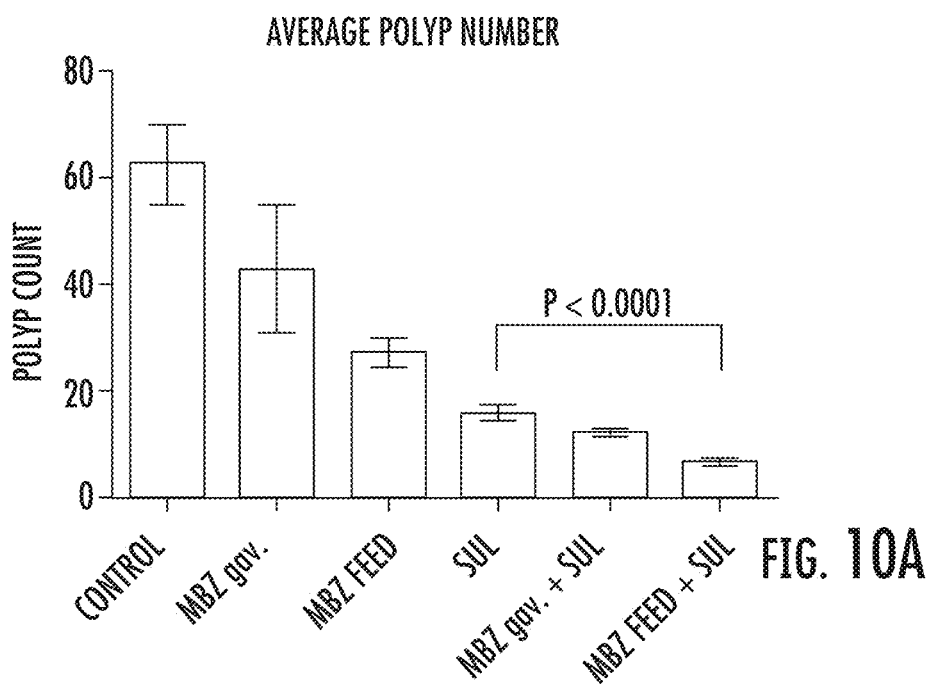
Figure 10B:
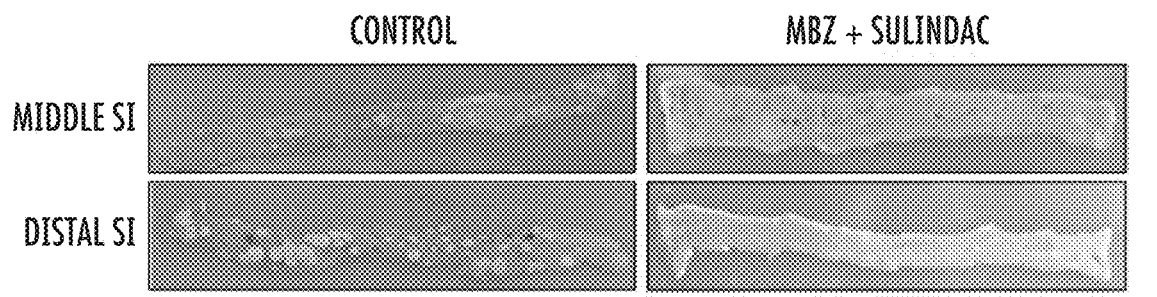
Figure 10C:
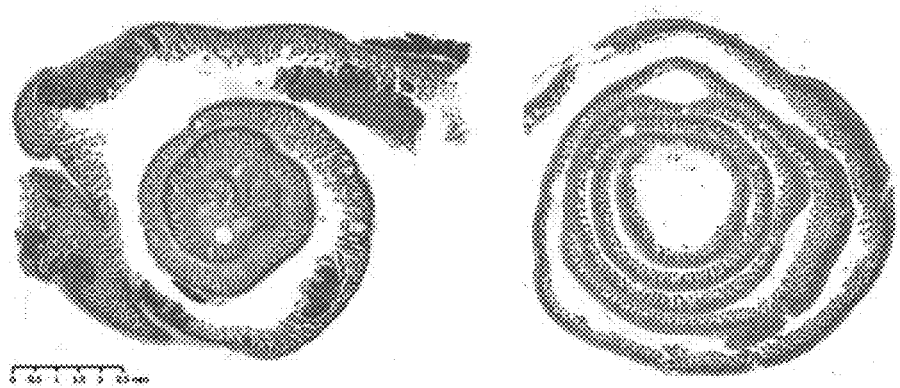

FIGS. 10A-10D. Mebendazole reduces the formation of polyps in the intestine of APC min/+ mice. At the end of the chemoprevention study, the small intestines and colon of APC min/+ mice were analyzed and the total number of polyps/mouse were averaged and compared across treatment groups (FIG. 10A); representative pictures of APC min/+ middle and distal small intestines from Control versus MBZ+Sulindac combination treatment (FIG. 10B); representative H&E stained swiss rolled intestine from Control (FIG. 10C, left) and MBZ+Sulindac combination treatment (FIG. 10C, right). Results are tabulated for number and location of polyps in each treatment group (FIG. 10D).

Figure 11A:
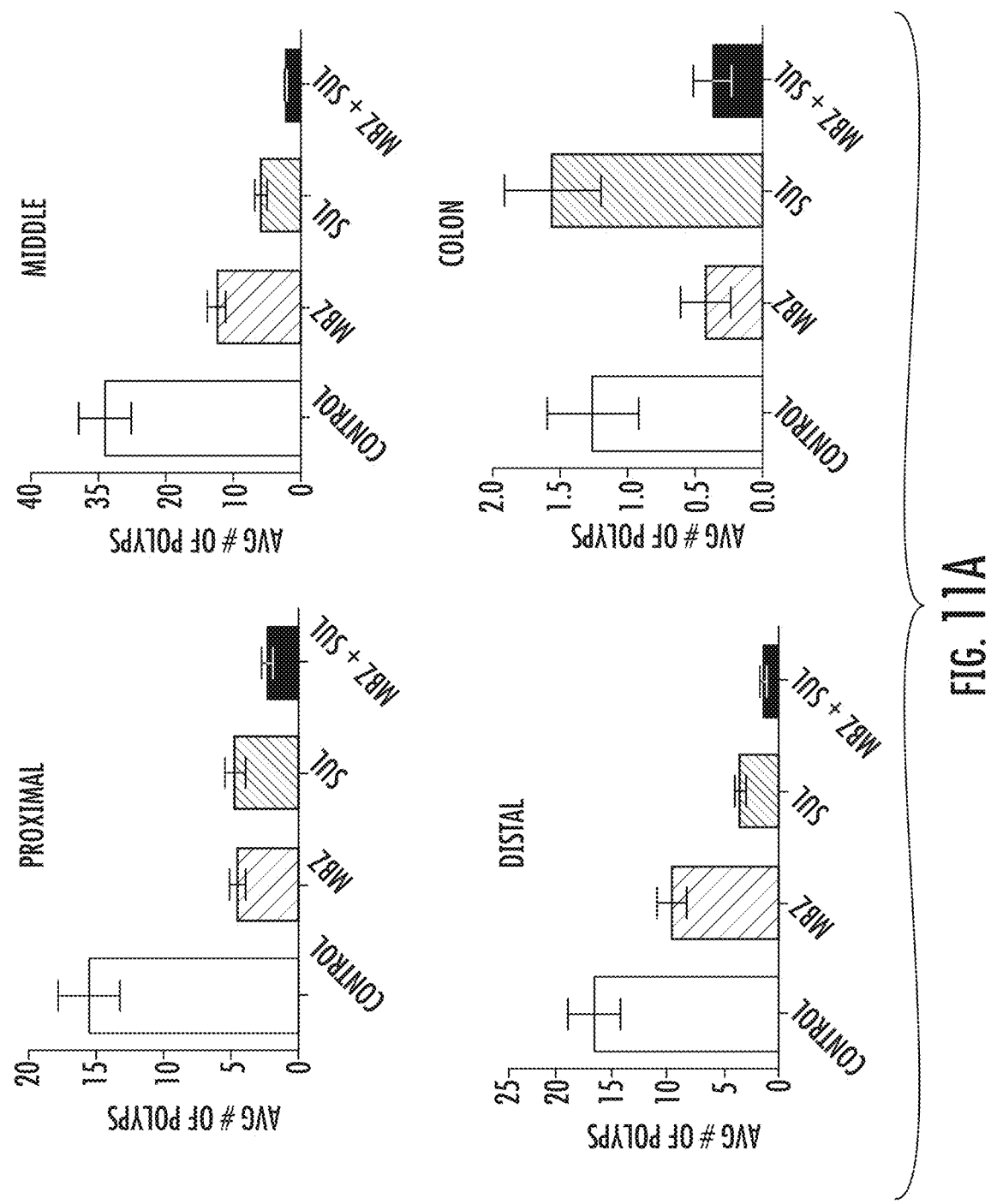
Figure 11B:
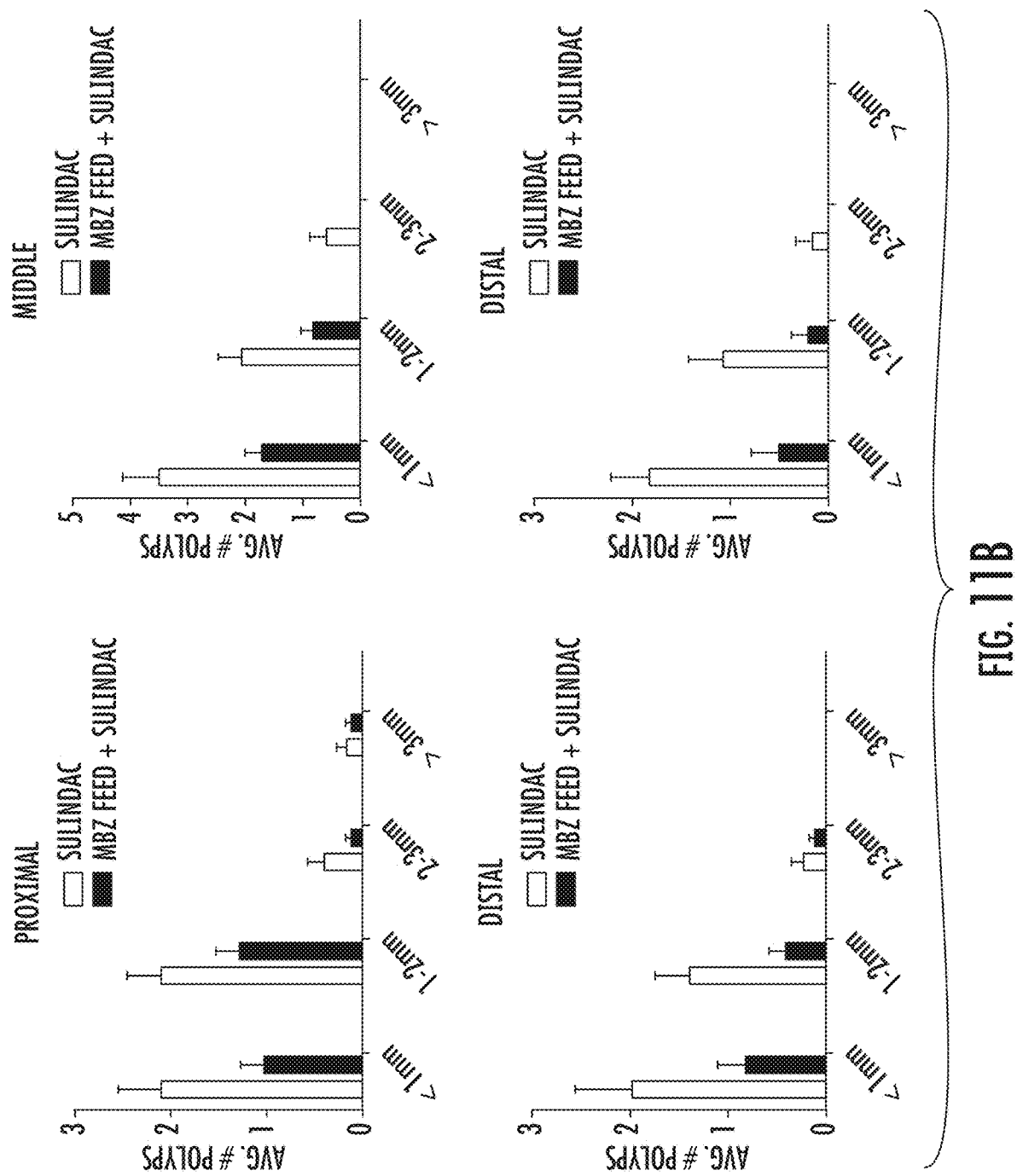

FIGS. 11A-11C. The combination of Mebendazole and Sulindac are synergistic reducing both the occurrence and size of tumors in all segments of the APC min/+ mouse intestine. The average number of polyps for each treatment group were graphed for the proximal, middle and distal small intestines and colon (FIG. 11A). Individual polyps were measured and categorized based on size. The average number of polyps for Sulindac versus the combiniation of MBZ+Sulindac were analyzed separately for each section of the intestine (FIG. 11B). Statistical analysis is shown in FIG. 11C.

Figure 12A:
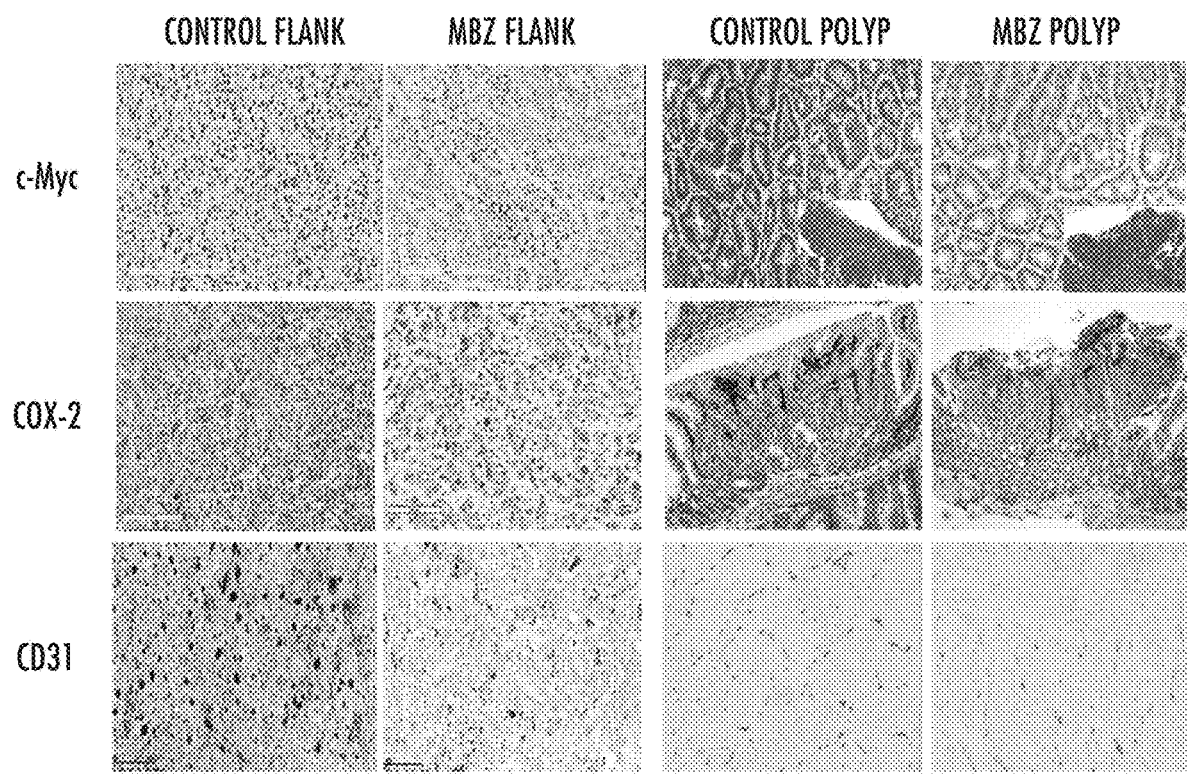
Figure 12B:
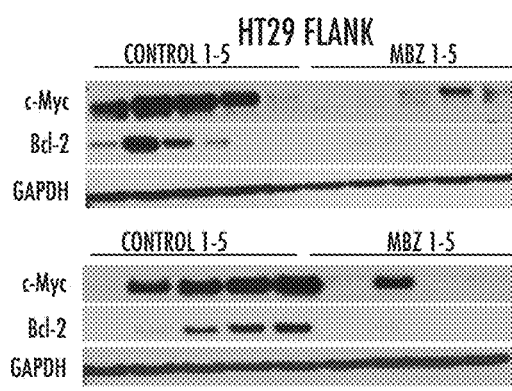
Figure 12C:
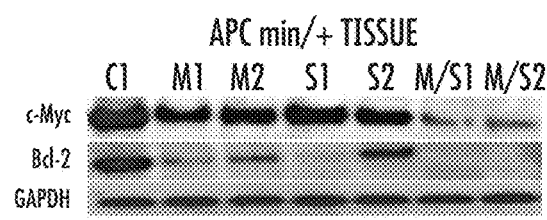

FIGS. 12A-12C. Mebendazole shows an anti-inflammatory and anti-angiogenesis effect in treated Min mouse polyps and in flank tumor xenografts. Paraffin-embedded sections of flank tumor tissue and APC min polyps were analyzed by immunohistochemistry using c-myc, COX-2, and CD31 antibodies. Representative pictures are shown for each (FIG. 12A). Lysates from individual HT29 (control n=5, MBZ n=5) and SW480 (control n=5, MBZ n=4) flank xenograft tissue were analyzed for c-myc and Bcl-2 protein expression (FIG. 12B) showing a reduction of these proteins in most cases with MBZ treatement. Similarly, in the polyps the min mouse there was a reduction of c-myc, and Bcl-2 in particular with the combination treatment. APC min/+ mouse intestinal tissue representing each treatment group were probed for c-myc and Bcl-2 (FIG. 12C). C1=control, M1, M2=MBZ treated, S1, S2=Sulindac treated, M/S1, M/S2=MBZ+Sulindac combination treatment. GAPDH was used as the loading control.

Figure 13:
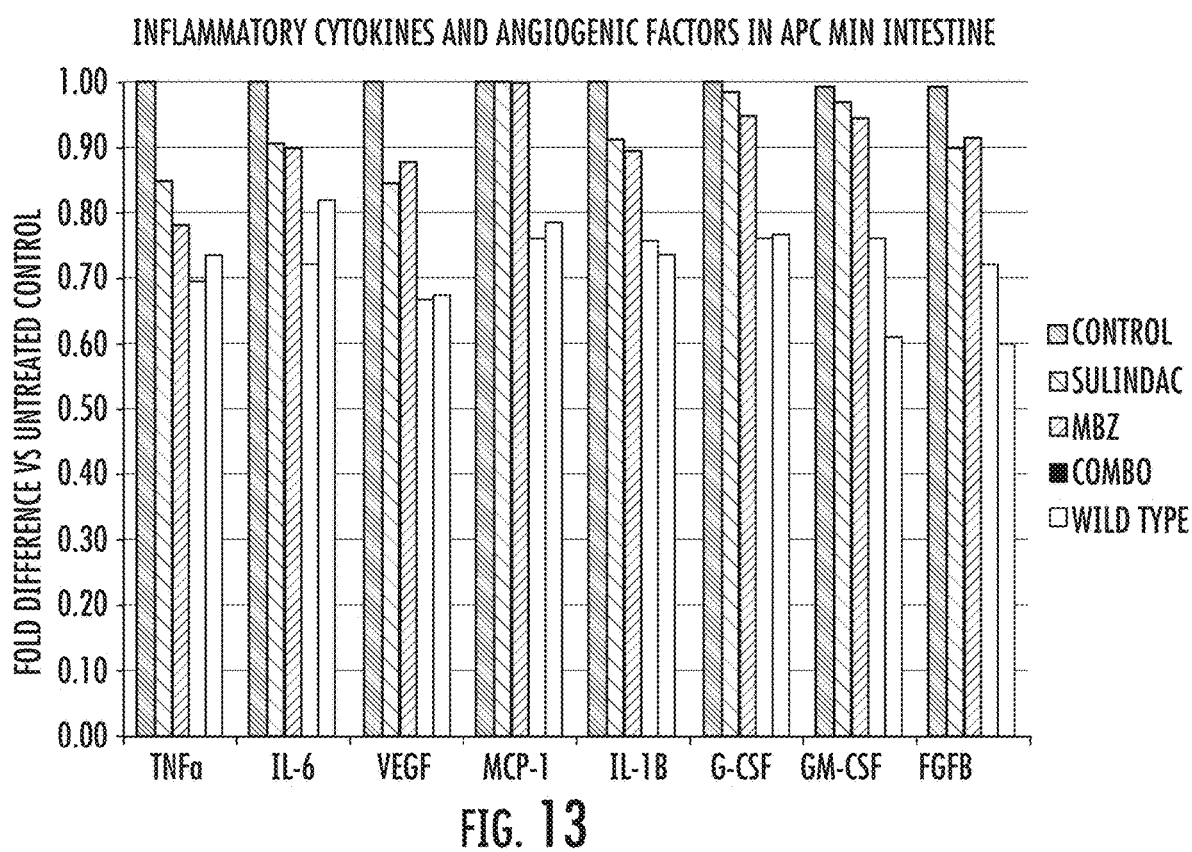

FIG. 13. The combiniation of Mebendazole plus Sulindac decrease inflammatory cytokines and angiogenic factors in the APC min/+ intestine more than either drug alone. A colorimetric Mouse ELISA strip reactive to TNFa, IL-6, VEGF, MCP-1, IL-1B, G-CSF, GM-CSF, and FGFβ was used to measure the reduction of pro-inflammatory markers in each treatment group. The relative absorbance values were averaged and the percent difference in values was compared to the results of the untreated control mice (n=3 mice averaged for each treatment group).

DETAILED DESCRIPTION OF THE INVENTION

The inventors have developed efficacious and safe formulations for treating tumors, particularly tumors of the brain, breast, and lung. Other tumors may also be treated including but not limited to colorectal, ovarian, sarcomas, gastric, esophageal, prostate, pancreatic, liver, and thyroid tumors.

Polymorph C of mebendazole has been found to be the most potent of the polymorphs for treating tumors. Often, however, it appears that the potency of a preparation decreases over time due to loss of polymorph C or conversion to other polymorphs. Preferably a preparation of mebendazole that is used in the invention will be at least 90% polymorph C. In some cases it may be at least 91%, 92%, 93%, 94%, 93%, 96%, 97%, 98%, or 99% polymorph C. The mebendazole may optionally be granulated. This provides a suitable formulation for adding to comestibles and providing a palatable medicament. It may also increase gastric absorption. Optionally the granulated form may be coated. This may increase the palatability of the medicament. Typical materials used for enteric coatings include fatty acids, waxes, shellac, plastics, and plant fibers. Any such enteric coatings used in the art may be used.

P-glycoprotein (P-gp), the permeability glycoprotein or plasma glycoprotein is an active, efflux, membrane bound transport protein pump. It is a member of ATP binding cassette (ABC) super family. It goes by many names including ABCB1, MDR1, PGY1, and CD243. It is involved in multidrug resistance in tumors. In that context it may be referred to as a multidrug resistant pump. Any inhibitor of P-gp can be used in formulations with mebendazole, including but not limited to elacridar, progesterone, gomasin A, piperine, apocyanin, amprenavir, quinidine, and valspodar. The P-gp inhibitor may be co-coated along with the mebendazole or the P-gp inhibitor may be uncoated or separately coated. The two agents may be administered at the same time, in combination or separately. The two agents may be delivered within days or weeks of each other as part of a combined regimen.

In some formulations and for some uses, such as prophylactic uses, polymorph C can be formulated with a non-steroidal anti-inflammatory drug. These include, without limitation, Aspirin, Choline and magnesium salicylates, Choline salicylate, Celecoxib, Dielofenac potassium, Dielofenac sodium, Dielofenac sodium with misoprostol, Diflunisal, Etodolac, Fenoprofen calcium, Flurbiprofen, Ibuprofen, Indomethacin, Ketoprofen, Magnesium salicylate, Meclofenamate sodium, Mefenamic acid, Meloxicam, Nabumetone, Naproxen, Naproxen sodium, Oxaprozin, Piroxicam Rofecoxib, Salsalate, Sodium salicylate, Sulindac, Tolmetin sodium, and Valdecoxib. The combination is potent in prophylactic effect.

Individuals who have higher risk of developing colorectal cancer are those with any of a variety of environmental, behavioral, and genetic factors. These include, without limitation, overweight or obese, physical inactivity, a diet that is high in red meats (such as beef, pork, lamb, or liver) and processed meats, smoking, heavy alcohol use, personal history of colorectal polyps or colorectal cancer, personal history of inflammatory bowel disease, family history of colorectal cancer or adenomatous polyps, family cancer syndromes, familial adenomatous polyposis (FAP), Lynch syndrome, attenuated FAP, Turcot syndrome, Peutz-Jeghers syndrome, MUTYH-associated polyposis, and type 2 diabetes. These individuals may benefit from the prophylaxis with mebendazole, in particular with polymorph C, and more particularly with combination therapies of mebendazole and non-steroidal anti-inflammatory drugs. The two agents may be administered at the same time, in combination or separately. The two agents may be delivered within days or weeks of each other as part of a combined regimen of prophylaxis. A racemic mixture of mebendazole or even a composition comprising more of polymorphs A or B than C may be used for prophylactic and/or therapeutic anti-cancer treatments.

Application of a formulation to food may encompass any means known in the art. Sprinkling, shaking, spraying, dowsing, or mixing, for example, can be used to apply the formulation to the food. Administration or dispensing of a formulation for oral ingestion may comprise, for example, delivering in a cup, on a plate, or directly into the mouth of the subject.

Brain tumors which may be treated include Astrocytoma; Atypical Teratoid Rhaboid Tumor (ATRT); Chondrosarcoma; Choroid Plexus; Craniopharyngioma; Cysts; Ependymoma; Germ Cell Tumor; Glioblastoma; Glioma; Hemangioma; Lipoma; Lymphoma; Medulloblastoma; Meningioma; Metastatic Brain Tumor; Neurofibroma; Neuronal & Mixed Neuronal-Glial Tumors; Oligoastrocytoma; Oligodendroglioma; Pineal Tumors; Pituitary Tumors; PNET; and Schwannoma.

Human tumors which may be treated with the formulations include Acute Lymphoblastic Leukemia (ALL); Acute Myeloid Leukemia (AML); Adolescents, Cancer in; Adrenocortical Carcinoma; Childhood; AIDS-Related Cancers; Kaposi Sarcoma; Lymphoma; Anal Cancer; Appendix Cancer; Astrocytomas, Childhood; Atypical Teratoid/Rhabdoid Tumor, Childhood, Central Nervous System; Basal Cell Carcinoma—see Skin Cancer (Nonmelanoma); Childhood; Bile Duct Cancer, Extrahepatic; Bladder Cancer; Childhood;

Bone Cancer; Ewing Sarcoma Family of Tumors; Osteosarcoma and Malignant Fibrous Histiocytoma; Brain Stem Glioma, Childhood; Brain Tumor; Astrocytomas, Childhood; Brain and Spinal Cord Tumors Treatment Overview, Childhood; Brain Stem Glioma, Childhood; Central Nervous System Atypical Teratoid/Rhabdoid Tumor, Childhood; Central Nervous System Embryonal Tumors, Childhood; Central Nervous System Germ Cell Tumors, Childhood; Craniopharyngioma, Childhood; Ependymoma, Childhood; Breast Cancer; Childhood; Male; Pregnancy, Breast Cancer and; Bronchial Tumors, Childhood; Burkitt Lymphoma—see Non-Hodgkin Lymphoma; Carcinoid Tumor; Childhood; Gastrointestinal; Carcinoma of Unknown Primary; Childhood; Cardiac (Heart) Tumors, Childhood; Central Nervous System; Atypical Teratoid/Rhabdoid Tumor, Childhood; Embryonal Tumors, Childhood; Germ Cell Tumor, Childhood; Lymphoma, Primary; Cervical Cancer; Childhood; Childhood Cancers; Chordoma, Childhood; Chronic Lymphocytic Leukemia (CLL); Chronic Myelogenous Leukemia (CML); Chronic Myeloproliferative Neoplasms; Colon Cancer; Colorectal Cancer; Childhood; Craniopharyngioma, Childhood; Cutaneous T-Cell Lymphoma—see Mycosis Fungoides and Sézary Syndrome; Duct, Bile, Extrahepatic; Ductal Carcinoma In Situ (DCIS); Embryonal Tumors, Central Nervous System, Childhood; Endometrial Cancer; Ependymoma, Childhood; Esophageal Cancer; Childhood; Esthesioneuroblastoma, Childhood; Ewing Sarcoma; Extracranial Germ Cell Tumor, Childhood; Extragonadal Germ Cell Tumor; Extrahepatic Bile Duct Cancer; Eye Cancer; Intraocular Melanoma; Retinoblastoma; Fallopian Tube Cancer—see Ovarian Epithelial, Fallopian Tube, and Primary Peritoneal Cancer; Fibrous Histiocytoma of Bone, Malignant, and Osteosarcoma; Gallbladder Cancer; Gastric (Stomach) Cancer; Childhood; Gastrointestinal Carcinoid Tumor; Gastrointestinal Stromal Tumors (GIST); Childhood; Germ Cell Tumor; Central Nervous System, Extracranial, Childhood; Extragonadal; Ovarian; Testicular; Gestational Trophoblastic Disease; Glioma—see Brain Tumor; Childhood Brain Stem; Hairy Cell Leukemia; Head and Neck Cancer; Childhood; Heart Cancer, Childhood; Hepatocellular (Liver) Cancer; Histiocytosis, Langerhans Cell; Hodgkin Lymphoma; Hypopharyngeal Cancer; Ilntraocular Melanoma; Islet Cell Tumors, Pancreatic Neuroendocrine Tumors; Kaposi Sarcoma; Kidney; Renal Cell; Wilms Tumor and Other Childhood Kidney Tumors; Langerhans Cell Histiocytosis; Laryngeal Cancer; Childhood; Leukemia; Acute Lymphoblastic (ALL); Acute Myeloid (AML); Chronic Lymphocytic (CLL); Chronic Myelogenous (CML); Hairy Cell; Lip and Oral Cavity Cancer; Liver Cancer (Primary); Childhood; Lung Cancer; Childhood; Non-Small Cell; Small Cell; Lymphoma; AIDS-Related; Burkitt—see Non-Hodgkin Lymphoma; Cutaneous T-Cell—see Mycosis Fungoides and Sézary Syndrome; Hodgkin; Non-Hodgkin; Primary Central Nervous System (CNS); Macroglobulinemia, Waldenström; Male Breast Cancer; Malignant Fibrous Histiocytoma of Bone and Osteosarcoma; Melanoma; Childhood; Intraocular (Eye); Merkel Cell Carcinoma; Mesothelioma, Malignant; Childhood; Metastatic Squamous Neck Cancer with Occult Primary; Midline Tract Carcinoma Involving NUT Gene; Mouth Cancer; Multiple Endocrine Neoplasia Syndromes, Childhood; Multiple Myeloma/Plasma Cell Neoplasm; Mycosis Fungoides; Myelodysplastic Syndromes; Myelodysplastic/Myeloproliferative Neoplasms; Myelogenous Leukemia, Chronic (CML); Myeloid Leukemia, Acute (AML); Myeloma, Multiple; Myeloproliferative Neoplasms, Chronic; Nasal Cavity and Paranasal Sinus Cancer; Nasopharyngeal Cancer; Childhood; Neuroblastoma; Non-Hodgkin Lymphoma; Non-Small Cell Lung Cancer; Oral Cancer; Childhood; Oral Cavity Cancer, Lip and; Oropharyngeal Cancer; Osteosarcoma and Malignant Fibrous Histiocytoma of Bone; Ovarian Cancer; Childhood; Epithelial; Germ Cell Tumor; Low Malignant Potential Tumor; Pancreatic Cancer; Childhood; Pancreatic Neuroendocrine Tumors (Islet Cell Tumors); Papillomatosis, Childhood; Paraganglioma; Childhood; Paranasal Sinus and Nasal Cavity Cancer; Parathyroid Cancer; Penile Cancer; Pharyngeal Cancer; Pheochromocytoma; Childhood; Pituitary Tumor; Plasma Cell Neoplasm/Multiple Myeloma; Pleuropulmonary Blastoma, Childhood; Pregnancy and Breast Cancer; Primary Central Nervous System (CNS) Lymphoma; Prostate Cancer; Rectal Cancer; Renal Cell (Kidney) Cancer; Renal Pelvis and Ureter, Transitional Cell Cancer; Retinoblastoma; Rhabdomyosarcoma, Childhood; Salivary Gland Cancer; Childhood; Sarcoma; Ewing; Kaposi; Osteosarcoma (Bone Cancer); Rhabdomyosarcoma; Soft Tissue; Uterine; Sézary Syndrome; Skin Cancer; Childhood; Melanoma; Merkel Cell Carcinoma; Nonmelanoma; Small Cell Lung Cancer; Small Intestine Cancer; Soft Tissue Sarcoma; Squamous Cell Carcinoma—see Skin Cancer (Nonmelanoma); Childhood; Squamous Neck Cancer with Occult Primary, Metastatic; Stomach (Gastric) Cancer; Childhood; T-Cell Lymphoma, Cutaneous—see Mycosis Fungoides and Sézary Syndrome; Testicular Cancer; Childhood; Throat Cancer; Thymoma and Thymic Carcinoma; Childhood; Thyroid Cancer; Childhood; Transitional Cell Cancer of the Renal Pelvis and Ureter; Unknown Primary, Carcinoma of; Childhood; Unusual Cancers of Childhood; Ureter and Renal Pelvis, Transitional Cell Cancer; Urethral Cancer; Uterine Cancer, Endometrial; Uterine Sarcoma; Vaginal Cancer; Childhood; Vulvar Cancer; Waldenström Macroglobulinemia; and Wilms Tumor.

Kits are means of packaging two or more items in a single container. The kit may comprise multiple internal containers to keep components separate. The kit may comprise instructions or other printed matter to facilitate use, such as standard curves. Information may also be provided on an electronic storage medium such as a disk or drive. Information may be provided by reference to a website. Additional components that are useful for treating cancers may also be provided. Tools for administration may be included. Vessels for mixing components may be provided in the kit.

Mebendazole can be prepared by any means known in the art. In one method, p-chlorotoluene is used as a starting material. See FIG. 8. Typically for purification, polymorph C is crystalized using methanol at room temperature. Mebendazole is commercially available.

In this study, we demonstrate that MBZ can reach the brain tissue in significant concentrations and with high brain to plasma ratios. Between 1 and 8 hours after the oral administration, MBZ-C maintained the brain levels above 0.767 µg/g (equivalent to 2.7 µM), with a $C_{max}$ of 2,016 µg/g (equivalent to 7.1 µM). These exceeded the $IC_{50}$ (4.3 µM) of MBZ on VEGFR2 kinase in vitro and the $IC_{50}$ (0.11-1 µM) in a series of glioma and medulloblastoma cell lines in tissue culture (3,4). Furthermore, MBZ-C emerged as the most efficient polymorph, achieving an $ACU_{0-24h}$ B/P ratio of 0.82. This is encouraging since temozolomide, the standard treatment for high-grade gliomas, was measured of having a B/P ratio of 0.408 in mice and a cerebrospinal fluid (CSF)/plasma ratio of 0.2 in human (21,22). In our study, the distributions of MBZ in the GL261 brain tumor and in the normal brain tissue did not differ significantly. It is worth mentioning that advanced growth of GL261 glioma results in substantial amount of blood in the tumor, similarly to other glioma models and a thorough perfusion was essential to eliminate the contamination of MBZ from the blood.

Among the three polymorphs, MBZ-A showed no efficacy in GL261 glioma model, explained by the very low plasma presence at only 19% of $AUC_{0-24\ h}$ measured with MBZ-C. MBZ-A's low bioavailability and inferior anti-tumor efficacy are in line with previous reports of its poor performance in anti-parasitic applications (10,12). In comparison, MBZ-B was able to reach 165% of MBZ-C's $AUC_{0-24\ h}$ in the plasma, while showing a similar brain concentration demonstrated by the measurement at 6 h. This could explain the elevated toxicity of MBZ-B in GL261 glioma-bearing mice as the anti-brain tumor efficacy remained essentially the same compared to MBZ-C. Thus, we suggest that MBZ-C is a better choice in brain tumor therapy. As a practical matter, the tablets made by MBZ-C should be stored under lower temperature (13), since the MBZ tablets of Teva brand may have lost its efficacy under the standard RT condition within 3 years likely due to the conversion to polymorph A, although we do not know the original concentration of polymorph C in these tablets that used to be efficacious in our previous study (3).

MBZ's small size (295 daltons) and lipophilic property favor brain penetration (2). It is remarkable that other benzimidazoles tested so far, such as albendazole, thiabendazole, flubendazole, oxifendazole and fenbendazole sharing similar physical properties, failed or only marginally improved the survival of GL261 glioma-bearing mice, even at higher doses than MBZ (Supplementary FIG. 1) (3). As we previously made the observation that fenbendazole in feed impaired the intake of the implantation of a medulloblastoma cell line in athymic nude mice (3), it only made a very marginal and statistically insignificant survival improvement in GL261 glioma model by gavaging 5 days after the implantation. There are several factors potentially contributing to the stark discrepancy in the brain tumor therapy with various benzimidazoles. For one as shown with MBZ polymorph A, low bioavailability likely due to the poor absorption could be detrimental to the therapeutic performance of this class of drugs. Second, the brain penetration of these benzimidazoles has not been well studied and could be insufficient for any significant therapeutic effects. Furthermore, MBZ has been implicated in inhibiting multiple tyrosine kinases in recent reports, whereas albendazole showed lack of such ability, indicating differences in anti-tumor mechanisms among benzimidazoles (4,7,8).

P-glycoprotein (P-gp, ABCB1) is an ATP-binding cassette (ABC) transporter and plays an important role in limiting drug uptake into the brain. (23) Elacridar is a $3^{rd}$ generation inhibitor of P-gp efflux transporters and also inhibits the breast cancer-resistant protein (BCRP, ABCG2) that is another key efflux transporter in BBB (24). Previous studies demonstrated that co-administration of elacridar in rodents has markedly increased by multiple folds the brain distribution of a number of cancer drugs, such as sunitinib, pazopanib, erlotinib and crizotinib, which were determined as the substrates of P-gp and ABCG2 by in vitro and animal studies (25-28). Furthermore, elacridar has been found safe in Phase I clinical trials (19). In this study, we investigated the combination of elacridar with MBZ to potentially enhance its therapeutic efficacy. We found that the combination greatly improved the survival in two orthotopic brain tumor models. However, in this limited study, the B/P ratio and brain $AUC_{0-8\ h}$ of MBZ did not show statistically significant differences with co-administration of elacridar, despite its ability to significantly increase survival in brain cancer bearing mice. When analyzing the metabolites, $MBZ-NH_2$, one of the two major metabolites in rodents and human (20), was significantly elevated in terms of B/P ratio (2.5 folds) and $AUC_{0-8\ h}$ (2.4 folds) as a result of co-administration of elacridar. Also noticeable is our finding that $MBZ-N_2$ was preferentially accumulated in the GL261 brain tumor vs the normal brain tissues. Although these data could indicate that $MBZ-NH_2$ is a potential substrate of P-gp and/or ABCG2, the significance of this finding is unclear at this point. A possible direct cytotoxic effect of $MBZ-NH_2$ appears unlikely as further testing displayed only a marginal cytotoxicity with cultured GL261 cells. However, increased toxicity through $MBZ-NH_2$'s preferential accumulation in the acidic tumor environment cannot be excluded and requires further investigations. Further investigations include the study of MBZ and elacridar interactions, particularly the potential substrate profile of efflux transporters with MBZ, in order to better understand and thereby improve the combination with MBZ.

MBZ-C is the most efficacious polymorph in brain tumor therapy. The combination of MBZ-C with elacridar, a p-glycoprotein inhibitor, can greatly improve efficacy. This combination may be used to treat, inter alia, high grade glioma and/or medulloblastoma. The combination may be co-administered or separately administered as part of a regimen of treatment.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods

Chemicals and Drugs

MBZ tablets (500 mg) from Janssen Pharmaceuticals (Pantelmin®) and Medley Pharmaceuticals were purchase from local pharmacies in Brazil in 2013 and stored at −20° C. freezer. MBZ tablets (100 mg) from Teva Pharmaceuticals USA were purchased from the Outpatient Pharmacy at the Johns Hopkins Hospital in 2011 and stored at room temperature (RT). Teva has discontinued MBZ in the US market since Oct. 2011. Aurochem Laboratories LTD. (Mumbai, India) manufactured MBZ tablets (500 mg) S2015 containing the current active pharmaceutical ingredient (API) that typically has mixed polymorphs, and S2017 (polymorph C) with specific API revealed. Aurochem also kindly supplied us with MBZ polymorph A, B and C. Elacridar (ELD; GF120918; N-(4-(2-(1,2,3,4-tetrahydro-6,7-dimethoxy-2-isoquinolinyl)ethyl)phenyl)-9,10-dihydro-5-methoxy-9-oxo-4-acridine carboxamide)) was purchased from Sigma (St. Louis, Mo., USA). Thiabendazole (TBZ), flubendazole (FLZ), oxifendazole (OXZ) and fenbendazole (FBZ) were purchased from Sigma (St. Louis, Mo., USA).

Cell Lines and Tissue Culture

Cell lines for this study were obtained as previously described: mouse glioma cell line GL261 and the human medulloblastoma xenograft D425Med (D425). (3,14) GL261 and D425 cells were maintained in DMEM media supplemented with 10% fetal bovine serum and antibiotics at 37° C. in humidified air containing 5% CO2. GL261-luc cells expressing firefly luciferase were described previously (3).

Infrared Spectrometry of MBZ Polymorphs

A Direct Detect™ infrared (IR) spectrometer was used (Millipore, Billerica, Mass., USA). MBZ powder or tablets ground to powder was mixed with water first, applied to the card and air dried following the manufacturer's instructions. The spectra of —C=O and —NH were analyzed and compared as described before. (9)

Intracranial Mouse Models

All animal studies were approved by the Animal Care and Use Committee (ACUC) of the Johns Hopkins University. The intracranial implantation of GL261-luc in the frontal lobe and D425 cells in the cerebellum of the mouse brain followed the procedure described before (3,4). Five days after tumor implantation, mice were gavaged with MBZ or the other benzimidazoles at 50 mg/kg five days a week. MBZ and other benzimidazoles were prepared by either mixing the power with PBS and sesame oil (1:1, v:v) (Sigma) or by grinding the tablets to powder and resuspending in the aforementioned PBS/sesame oil mixture. Elacridar was prepared as a 10 mg/ml suspension in 0.5% hydroxypropylmethylcellulose and 0.5% Tween 80 in PBS similarly as described before (15).

MBZ Pharmacokinetic Studies

Female C57BL6 mice, 5-6 weeks of age, were purchased from NCI. Animal experimentation was conducted under an approved IACUC protocol and complied with local and national guidelines. All MBZ polymorphs and tablets were administered by oral gavage at a dose of 50 mg/kg. Elacridar was administered by oral gavage at 50 mg/kg 2 hours prior to the administration of MBZ-C. Mice (3 animals/time point) were first anesthetized via intraperitoneal injection of 60 μl of a stock solution containing ketamine hydrochloride (75 mg/kg) (100 mg/ml; Ketamine HCl; Abbot Laboratories, Chicago, Ill., USA) and xylazine (7.5 mg/kg) (100 mg/ml; Xyla-ject®, Phoenix Pharmaceutical, St. Joseph, Mo., USA) in a sterile 0.9% NaCl solution. Then the blood samples were taken by puncturing and aspirating from the left heart ventricle. Blood samples were mixed with 5 mM EDTA and centrifuged at 10000 g for 5 min to obtain the plasma for further analysis.

For brain distribution studies, mice were perfused under anesthesia with 20 ml ice-cold saline supplemented with 20 μl of 0.02% heparin by injecting slowly into the left heart ventricle using a 20 gauge needle. The right atrium was cut open before to allow the blood outflow. The yellow color of kidney indicated a good perfusion quality that was essential to deplete blood from the brain tissue. In GL261 tumor-bearing mice, GL261 tumor was distinguished from the normal brain by easily recognizable differences in color and shade. GL261 tumor was separated with a scalpel and the normal brain tissue was cut from the contralateral hemisphere. All brain samples were weighed and stored at −80° C. before processing.

Blood, brain and brain tumor tissues were harvested as a function of time after MBZ administration. To compare the pharmacokinetics of MBZ polymorphs, three cohorts of mice each were administered a single dose of 50 mg/kg by oral gavage. For the initial comparison studies, plasma samples were obtained at 1, 2.5, 4, 6, 8, 15, and 24 hours after MBZ administration while brain tissue was only collected at 6 hours. For the comparison studies of polymorph C with or without ELD, plasma and brain tissue samples were obtained at 2.5, 4, and 8 hours after MBZ administration. Brain tumor tissue samples were also obtained for polymorph C alone.

Measurement of MBZ and Metabolites

MBZ and the two metabolites, 2-amino-5-benzoyl-benzimidazole (MBZ-NH$_2$, CAS 52329-60-9) and rac dihydro mebendazole (MBZ-OH, CAS 60254-95-7), were quantified in plasma, brain and brain tumor tissue. Tissue homogenates were prepared at a concentration of 200 mg/ml in plasma prior to extraction. Mebendazole and metabolites were extracted from 50 μl of plasma or tissue homogenates with 0.1 ml of methanol containing 0.5 μg/ml of the internal standard A620223.69. After centrifugation, the supernatant (60 μl) was mixed with water (40 μl) and then transferred into autosampler vials. Separation was achieved with an Atlantis dC18 (2.1×100 mm, 3 μm) column at room temperature with methanol/water mobile phase (60:40, v:v) containing 0.1% formic acid using isocratic flow at 0.25 ml/min for 5 minutes. The analytes were monitored using an AB Sciex triple quadrapole™ 5500 mass-spectrometric detector (Applied Biosystems, Foster City, Calif., USA) using electrospray ionization operating in positive mode. The spectrometer was programmed to allow the [MH+] ions of MBZ, MBZ-NH$_2$, MBZ-OH, and A620223.69 at m/z 296.0, 238.0, 298.0, and 287.2, respectively to pass through the first quadrupole (Q1) and into the collision cell (Q2). The daughter ions for MBZ (m/z 263.9), MBZ-NH$_2$ (m/z 105.1), MBZ-OH (m/z 266.0), and A620223.69 (m/z 124.1) were monitored through the third quadrupole (Q3). Calibration curves for MBZ and metabolites were computed using the area ratio peak of the analysis to the internal standard by using a quadratic equation with a 1/x weighting function over the range of 5 to 500 ng/ml (MBZ) and 1 to 500 ng/ml (metabolites) with dilutions of up to 1:100 (v:v). If one or more concentrations were below limits of quantification, a value of ½ the limit of quantification was assigned for pharmacokinetic calculations. If two consecutive time points were below limits of quantification, the last one was excluded from the analysis.

Mean plasma and brain concentrations were calculated at each time point for both MBZ and its metabolites. 1.045 g/ml was used as the average wet rodent brain tissue density (16). Pharmacokinetic parameters were calculated from mean MBZ and its metabolites concentration-time data using noncompartmental methods as analyzed in Phoenix® WinNonlin® version 6.3 (Pharsight Corp., Mountain View, Calif.). $C_{max}$ and $T_{max}$ were the observed values from the mean concentration data. The $AUC_{last}$ was calculated using the log-linear trapezoidal method. $\lambda_z$ was determined from the slope of the terminal phase of the concentration-time profile. The terminal half-life ($T_{1/2}$) was determined by dividing 0.693 by $\lambda_z$. If the $r^2$ of $\lambda_z$ was <0.9, the $T_{1/2}$ was not reported. Relative systemic exposure to MBZ was calculated using the $AUC_{last}$: Metabolites $AUC_{last}$/MBZ $AUC_{last}$. Relative systemic exposure in brain or brain tumor compared with plasma was calculated using the $AUC_{last}$: Brain or Brain Tumor $AUC_{last}$/Plasma $AUC_{last}$.

Statistical Analysis

Animal survival data were analyzed by GraphPad Prism 5.0. The p-values were determined by a Mantel-Cox test. A p-value under 0.05 was accepted as statistically significant.

For the pharmacokinetic studies comparing the polymorphs or administration with ELD, the Method of Bailer was used to estimate the variance of $AUC_{last}$ given the calculated variance of the mean concentration at each time point (17). This was then followed by a pairwise comparison using a Z-test to determine whether there was a significant difference between MBZ exposure as expressed by $AUC_{last}$ (18). Comparisons of individual data were conducted using the nonparametric Wilcoxon signed rank test with post-hoc analysis using an All Pairs Tukey-Kramer test. The level of significance was P<0.05.

EXAMPLE 2

Polymorph C was Most Effective for Treating Brain Tumors in Mice

We examined the polymorph content of several commercially available tablets (Janssen, Medley and Teva) and two made to order tablets (Aurochem S2015 used the current API that typically has mixed polymorphs and S2017 was specified as pure MBZ-C) by comparing their IR profiles with the individual MBZ polymorphs (FIGS. 1A and B). Based on the IR peaks of —C=O and —NH bonds, we determined that the Janssen and Medley tablets were made of mainly MBZ-C as well as the Aurochem S2017. Aurochem S2015 and Teva tablets that have been stored at RT for 2 years showed mainly the profiles of MBZ-A. As a control, polymorph A, B and C were dissolved in DMSO and incubated individually with GL261 glioma cells, which showed equal cytotoxicity (data not shown).

MBZ-A appeared to be ineffective in treating intracranial GL261 glioma-bearing mice, while MBZ-C displayed the best efficacy (FIG. 1C). Although MBZ-B showed a similar survival to MBZ-C, it caused more toxicity with 1 treatment-related death among 6 treated mice (FIG. 1C). The efficacy data reflected the polymorph composition of MBZ tablets well in the sense that S2015 was ineffective and other tablets made of MBZ-C all showed significant efficacy by extending the mean survival to 42-50 days from 29 days of the control group (FIG. 1E).

EXAMPLE 3

MBZ Reached the Brain at Significant Levels

Following an oral dosing of 50 mg/kg, MBZ-C achieved a plasma $AUC_{0-24\ h}$ of 16,039 h*ng/ml (FIG. 2A and Table 1A). In comparison, MBZ-B reached a plasma $AUC_{0-24\ h}$ of 26,474 h*ng/ml, while MBZ-A plasma $AUC_{0-24\ h}$ reached only 3,052 h*ng/ml, by far the lowest among all three polymorphs (P<0.05 for $AUC_{0-24\ h}$ with MBZ-B>-C>-A; Table 1A). Measurements of brain tissues following a thorough perfusion revealed significant presence of MBZ-C over a time course, correlating closely with the plasma MBZ levels with a brain/plasma (B/P) ratio of 0.75 on average that remained relatively stable during the 8 hours (FIGS. 2B-2C). Comparing the polymorphs at 6 h following oral gavage, we found MBZ-C and -B achieved similar brain levels, despite MBZ-B's higher levels and $AUC_{0-24\ h}$ in the plasma (FIG. 2D and FIG. 6, Table 1A), resulting in a slightly favorable mean B/P ratio of MBZ-C over MBZ-B (0.80 for C vs 0.64 for B and 0.29 for C, p=0.055) (FIG. 2E). This corroborates well with the efficacy data in FIG. 1C, where MBZ-B and -C demonstrated similar survival benefit in GL261 model (mean survival: 45 days of MBZ-B vs 48.5 days of MBZ-C). However, it is notable that MBZ-B displayed greater toxicity, resulting in early death of one mouse among the six treated animals (FIG. 2D). Analysis of the GL261 brain tumor and the contralateral brain tissues indicated equal distribution of MBZ-C in the brain tumor and the normal brain tissues (FIG. 2D).

EXAMPLE 4

Pharmacokinetics of MBZ Metabolites

Figure 3A:
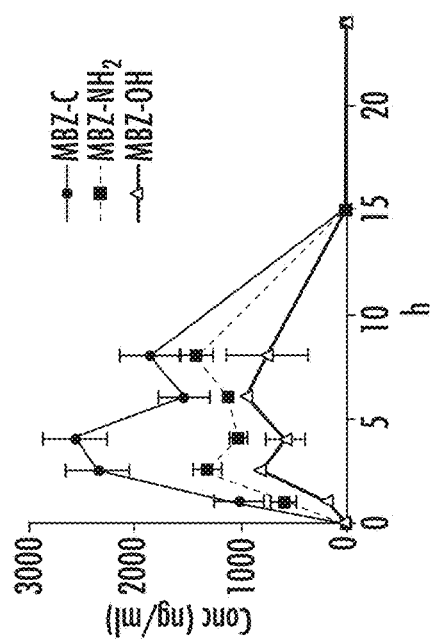
Figure 3C:
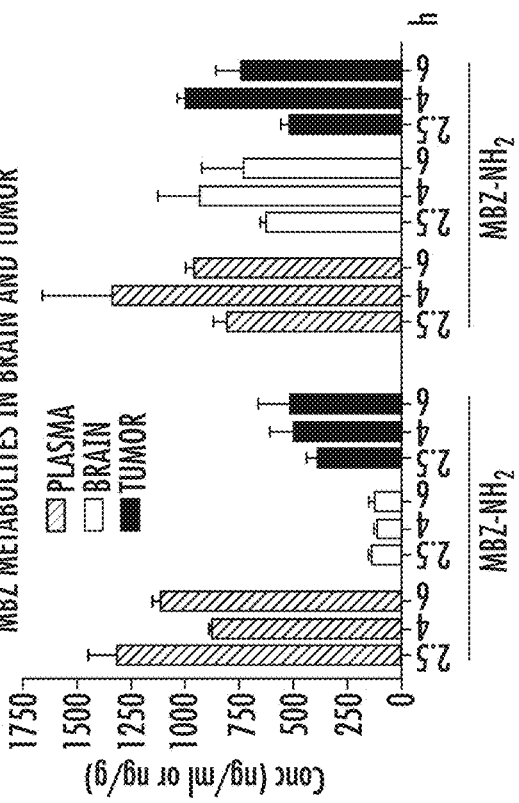

We determined the plasma levels of the major metabolites $MBZ-NH_2$ and MBZ-OH of MBZ polymorphs (P<0.05 for $AUC_{0-24\ h}$ of $MBZ-NH_2$ with MBZ-B>C>A; P<0.05 for $AUC_{0-24\ h}$ of MBZ-OH with MBZ-B and C>A; Table 1A). The levels of MBZ-C's metabolites in plasma and brain generally followed the same pattern of MBZ-C's concentration (FIGS. 3A and B). $MBZ-NH_2$ showed higher levels than MBZ-OH in the plasma (FIG. 3A), with an $AUC_{0-24\ h}$ of 10,516 h*ng/ml compared to 5,781 h*ng/ml of MBZ-OH (Table 1A). Notably, in a reversed pattern, $MBZ-NH_2$ was measured at much lower levels than MBZ-OH in the brain in terms of $C_{max}$ and $AUC_{0-24\ h}$ (FIG. 3B and Table 1A). Interestingly, in GL261 glioma, $MBZ-NH_2$ reached significantly higher levels than in the contralateral brain (FIG. 3C). In order to elucidate the anti-tumor role of MBZ metabolites, we compared the $IC_{50}$ of MBZ, MBZ-OH and $MBZ-NH_2$ in GL261 cells and determined $MBZ-NH_2$ is the least cytotoxic derivative of MBZ in vitro (FIG. 3D).

EXAMPLE 5

Combination of MBZ with Elacridar

Achieving a sufficient therapeutic concentration in the tumor and the surrounding brain tissue is a critical challenge that is faced by almost all brain cancer therapies. Four hours after oral administration, we found MBZ-C brain concentration peaked at 2,016 ng/g (equivalent to 7.1 µM) (Table 1A), which was well above the $IC_{50}$s of cultured glioma and medulloblastoma cells (0.11-1 µM) and also above MBZ's inhibitory $IC_{50}$ with VEGFR2 kinase at 4.3 µM in vitro (3,4). The relatively high brain concentration might help explain MBZ efficacy in brain tumor models. Next, we reasoned that a further increase in the brain distribution of MBZ would be desirable as it may increase therapeutic efficacy. Aside from a pure mechanical barrier, the BBB employs active efflux mechanisms to limit drug entry such as P-glycoprotein (P-gp). Elacridar (ELD) is a potent third-generation inhibitor that inhibits P-gp as well as breast cancer resistance protein (BCRP) and co-administration of elacridar has increased the brain penetration of several drugs (15,19). We first examined the cytotoxicity of elacridar in GL261 mouse glioma cells and determined the $IC_{50}$ to be 5.8 µM (FIG. 4A). Combining elacridar with 0.25 µM MBZ only marginally increased the cytotoxicity in vitro (FIG. 4B). Oral administration of 50 mg/kg elacridar two hours prior to MBZ-C did not significantly change the brain concentration of MBZ in terms of $AUC_{0-8h}$, while B/P ratio average of 2.5, 4 and 8 h was shifted slightly higher from 0.75 to 1.03, which, however, was not statistically significant (Table 1B and FIG. 4C). Interestingly, this was accompanied by a significant increase in $MBZ-NH_2$ along with an elevation of the B/P ratio from 0.12 to 0.30 in the brain when treated with a combination of elacridar and MBZ-C (Table 1B).

EXAMPLE 6

Combination with Elacridar Improved the Treatment of MBZ

Combination therapy of elacridar and MBZ increased the survival benefit in GL261 syngeneic glioma and D425 xenograft medulloblastoma models (FIG. 5). This was achieved by adding 7 or 14 days of 50 mg/kg elacridar treatment to the standard MBZ (MBZ-C) regimen of 50 mg/kg. Specifically, in GL261, combination therapy improved the median survival to 92.5 and 110.5 days dependent on the treatment length, which is a stark increase from 53 days of MBZ alone as well as 29.5 days (control) and 34 days (elacridar alone) (FIG. 5B). Similarly, in the orthotopic D425 medulloblastoma xenograft model, the combination of elacridar with MBZ increased the median survival to 77 days (FIG. 5D). This is a significant improvement from MBZ only treatment with 53 days of survival and elacridar alone, which showed a marginal survival benefit of 9 days in this particular animal model.

A prolonged treatment course with elacridar and MBZ was attempted, however, increased toxicity such as severe weight loss and mortality limited those studies (data not shown).

REFERENCES

The disclosure of each reference cited is expressly incorporated herein.
1. Bai R Y, Staedtke V, Riggins G J. Molecular targeting of glioblastoma: Drug discovery and therapies. Trends Mol Med 2011; 17: 301-12.
2. Chico L K, Van Eldik L J, Watterson D M. Targeting protein kinases in central nervous system disorders. Nat Rev Drug Discov 2009; 8: 892-909.
3. Bai R Y, Staedtke V, Aprhys C M, Gallia G L, Riggins G J. Antiparasitic mebendazole shows survival benefit in 2 preclinical models of glioblastoma multiforme. Neuro Oncol 2011; 13: 974-82.
4. Bai R Y, Staedtke V, Rudin C M, Bunz F, Riggins G J. Effective treatment of diverse medulloblastoma models with mebendazole and its impact on tumor angiogenesis. Neuro Oncol 2014, Sep. 24; Epub ahead of print.
5. Doudican N, Rodriguez A, Osman I, Orlow S J. Mebendazole induces apoptosis via Bcl-2 inactivation in chemoresistant melanoma cells. Mol Cancer Res 2008; 6: 1308-15.
6. Doudican N A, Byron S A, Pollock P M, Orlow S J. XIAP downregulation accompanies mebendazole growth inhibition in melanoma xenografts. Anticancer Drugs 2013; 24: 181-8.
7. Dakshanamurthy S, Issa N T, Assefnia S, et al. Predicting new indications for approved drugs using a proteochemometric method. J Med Chem 2012; 55: 6832-48.
8. Nygren P, Fryknas M, Agerup B, Larsson R. Repositioning of the anthelmintic drug mebendazole for the treatment for colon cancer. J Cancer Res Clin Oncol 2013; 139: 2133-40.
9. Liebenberg W, Dekker T G, Lotter A P, de Villiers M M. Identification of the mebendazole polymorphic form present in raw materials and tablets available in South Africa. Drug Dev Ind Pharm 1998; 24: 485-8.
10. Rodriguez-Caabeiro F, Criado-Fornelio A, Jimenez-Gonzalez A, et al. Experimental chemotherapy and toxicity in mice of three mebendazole polymorphic forms. Chemotherapy 1987; 33: 266-71.
11. Swanepoel E, Liebenberg W, de Villiers M M. Quality evaluation of generic drugs by dissolution test: changing the USP dissolution medium to distinguish between active and non-active mebendazole polymorphs. Eur J Pharm Biopharm 2003; 55: 345-9.
12. Charoenlarp P, Waikagul J, Muennoo C, Srinophakun S, Kitayaporn D. Efficacy of single-dose mebendazole, polymorphic forms A and C, in the treatment of hookworm and Trichuris infections. Southeast Asian J Trop Med Public Health 1993; 24: 712-6.
13. Brits M, Liebenberg W, de Villiers M M. Characterization of polymorph transformations that decrease the stability of tablets containing the WHO essential drug mebendazole. J Pharm Sci 2010; 99: 1138-51.
14. Bai R Y, Staedtke V, Lidov H G, Eberhart C G, Riggins G J. OTX2 Represses Myogenic and Neuronal Differentiation in Medulloblastoma Cells. Cancer Res 2012; 72: 5988-6001.
15. Sane R, Agarwal S, Elmquist W F. Brain distribution and bioavailability of elacridar after different routes of administration in the mouse. Drug Metab Dispos 2012; 40: 1612-9.
16. DiResta G R, Lee J, Lau N, Ali F, Galicich J H, Arbit E. Measurement of brain tissue density using pycnometry. Acta Neurochir Suppl (Wien) 1990; 51: 34-6.
17. Bailer A J. Testing for the equality of area under the curves when using destructive measurement techniques. J Pharmacokinet Biopharm 1988; 16: 303-9.
18. Yuan J. Estimation of variance for AUC in animal studies. J Pharm Sci 1993; 82: 761-3.
19. Werle M, Takeuchi H, Bernkop-Schnurch A. New-generation efflux pump inhibitors. Expert Rev Clin Pharmacol 2008; 1: 429-40.
20. Dayan A D. Albendazole, mebendazole and praziquantel. Review of non-clinical toxicity and pharmacokinetics. Acta Trop 2003; 86: 141-59.
21. Zhou Q, Gallo J M. Differential effect of sunitinib on the distribution of temozolomide in an orthotopic glioma model. Neuro Oncol 2009; 11: 301-10.
22. Ostermann S, Csajka C, Buclin T, et al. Plasma and cerebrospinal fluid population pharmacokinetics of temozolomide in malignant glioma patients. Clin Cancer Res 2004; 10: 3728-36.
23. Redzic Z. Molecular biology of the blood-brain and the blood-cerebrospinal fluid barriers: similarities and differences. Fluids Barriers CNS 2011; 8: 3.
24. Shukla S, Ohnuma S, Ambudkar S V. Improving cancer chemotherapy with modulators of ABC drug transporters. Curr Drug Targets 2011; 12: 621-30.
25. Tang S C, Lagas J S, Lankheet N A, et al. Brain accumulation of sunitinib is restricted by P-glycoprotein (ABCB1) and breast cancer resistance protein (ABCG2) and can be enhanced by oral elacridar and sunitinib coadministration. Int J Cancer 2012; 130: 223-33.
26. Minocha M, Khurana V, Qin B, Pal D, Mitra A K. Enhanced brain accumulation of pazoparnib by modulating P-gp and Bcrp1 mediated efflux with canertinib or erlotinib. Int J Pharm 2012; 436: 127-34.
27. Agarwal S, Manchanda P, Vogelbaum M A, Ohlfest J R, Elmquist W F. Function of the blood-brain barrier and restriction of drug delivery to invasive glioma cells: findings in an orthotopic rat xenograft model of glioma. Drug Metab Dispos 2013; 41: 33-9.
28. Tang S C, Nguyen L N, Sparidans R W, Wagenaar E, Beijnen J H, Schinkel A H. Increased oral availability and brain accumulation of the ALK inhibitor crizotinib by coadministration of the P-glycoprotein (ABCB1) and breast cancer resistance protein (ABCG2) inhibitor elacridar. Int J Cancer 2014; 134: 1484-94.

We claim:
1. A method of treating a brain tumor in a human subject comprising:
administering to the subject a sufficient amount of a pharmaceutical formulation comprising mebendazole wherein at least 90% of the mebendazole in the formulation is polymorph C and the pharmaceutical formulation is granulated.

2. The method of claim 1 wherein the brain tumor is a medulloblastoma.

3. The method of claim 1 wherein the brain tumor is a glioma.

4. The method of claim 1 wherein the tumor has a multidrug resistant pump.

5. The method of claim 1 wherein the subject is administered one or more non-steroidal anti-inflammatory drug or an inhibitor of P-glycoprotein.

6. The method of claim 1 wherein the one or more non-steroidal drug or an inhibitor of P-glycoprotein and the pharmaceutical formulation comprising mebendazole are administered at the same time.

7. The method of claim 5 or 6 wherein the inhibitor of P-glycoprotein is elacridar.

* * * * *